(12) United States Patent
Gerbec et al.

(10) Patent No.: US 6,875,239 B2
(45) Date of Patent: Apr. 5, 2005

(54) MODULAR PROSTHESIS FOR REPLACING BONE AND METHOD

(75) Inventors: Daniel E. Gerbec, Logan, UT (US); T. Wade Fallin, Hyde Part, UT (US); Patrick M. White, Downingtown, PA (US)

(73) Assignee: Medicinelodge, Inc., Logan, UT (US)

( * ) Notice: Subject to any disclaimer, the term of this patent is extended or adjusted under 35 U.S.C. 154(b) by 224 days.

(21) Appl. No.: 10/132,671

(22) Filed: Apr. 25, 2002

(65) Prior Publication Data

US 2003/0204266 A1 Oct. 30, 2003

(51) Int. Cl.⁷ .................................................. A61F 2/38
(52) U.S. Cl. .................................................. 623/23.15
(58) Field of Search ................. 623/22.11, 23.11–23.38

(56) References Cited

U.S. PATENT DOCUMENTS

| | | |
|---|---|---|
| 2,682,265 A | 6/1954 | Collison |
| 2,785,673 A | 3/1957 | Anderson |
| 3,806,957 A | 4/1974 | Shersher |
| 3,848,272 A | 11/1974 | Noiles |
| 3,875,593 A | 4/1975 | Shersher |
| 3,906,550 A | 9/1975 | Rostoker et al. |
| 3,943,576 A | 3/1976 | Sivash |
| 3,987,499 A | 10/1976 | Scharbach et al. |
| 4,016,651 A | 4/1977 | Kawahara et al. |
| 4,051,559 A | 10/1977 | Pifferi |
| 4,086,701 A | 5/1978 | Kawahara et al. |
| 4,259,072 A | 3/1981 | Hirabayashi et al. |
| 4,304,011 A | 12/1981 | Whelan, III |
| 4,404,691 A | 9/1983 | Buning et al. |
| 4,520,511 A | 6/1985 | Gianezio et al. |
| 4,578,081 A | 3/1986 | Harder et al. |
| 4,619,659 A | 10/1986 | Witzel |
| 4,624,673 A | 11/1986 | Meyer |
| 4,676,797 A | 6/1987 | Anapliotis et al. |
| 4,714,471 A | 12/1987 | Grundei |
| 4,790,854 A | 12/1988 | Harder et al. |
| 4,822,366 A | 4/1989 | Bolesky |
| 4,842,606 A | 6/1989 | Kranz et al. |
| 4,846,839 A | 7/1989 | Noiles |
| 4,851,007 A | 7/1989 | Gray |

(Continued)

FOREIGN PATENT DOCUMENTS

| | | |
|---|---|---|
| DE | 32 05 577 A1 | 10/1982 |
| DE | 33 40 767 A1 | 5/1985 |
| DE | 40 31 520 A1 | 4/1992 |
| EP | 0 000 549 A1 | 2/1979 |
| EP | 0 201 407 A1 | 11/1986 |
| EP | 0 283 706 A1 | 9/1988 |
| EP | 0 336 774 A1 | 10/1989 |
| EP | 0 336 774 B1 | 10/1989 |
| EP | 0 359 457 A1 | 3/1990 |
| EP | 0 376 658 A2 | 7/1990 |
| EP | 0 433 121 A1 | 6/1991 |
| EP | 0 495 340 A1 | 7/1992 |
| EP | 0 556 997 A1 | 8/1993 |
| EP | 0 714 645 A1 | 6/1996 |
| EP | 0 714 645 B1 | 6/1996 |

(Continued)

*Primary Examiner*—John J. Wilson
*Assistant Examiner*—Michael B. Priddy
(74) *Attorney, Agent, or Firm*—Workman Nydegger

(57) ABSTRACT

A modular prosthesis for replacing a portion of a bone having an articulating end includes a neck having a bore extending therethrough, a body having a bore extending therethrough, and an elongated stem. A proximal end of the stem is received within the bore of the body and the bore of the neck so that at least a self-locking taper connection or a press fit connection is formed between the stem and each of the neck and the body.

35 Claims, 22 Drawing Sheets

U.S. PATENT DOCUMENTS

| | | | |
|---|---|---|---|
| 4,878,917 A | 11/1989 | Kranz et al. | |
| 4,908,032 A | 3/1990 | Keller | |
| 4,917,530 A | 4/1990 | Engelhardt et al. | |
| 4,919,678 A | 4/1990 | Kranz | |
| 4,936,853 A | 6/1990 | Fabian et al. | |
| 4,938,773 A | 7/1990 | Strand | |
| 4,985,037 A | 1/1991 | Petersen | |
| 4,995,883 A | 2/1991 | Demane et al. | |
| 5,002,578 A | 3/1991 | Luman | |
| 5,002,581 A | 3/1991 | Paxson et al. | |
| 5,019,108 A | 5/1991 | Bertin et al. | |
| 5,026,280 A | 6/1991 | Dürr et al. | |
| 5,035,712 A | 7/1991 | Hoffman | |
| 5,058,936 A | 10/1991 | Kapgan et al. | |
| 5,080,676 A | 1/1992 | May | |
| 5,080,685 A | 1/1992 | Bolesky et al. | |
| 5,108,437 A | 4/1992 | Kenna | |
| 5,108,452 A | 4/1992 | Fallin et al. | |
| 5,133,760 A | 7/1992 | Petersen et al. | |
| 5,133,771 A | 7/1992 | Duncan et al. | |
| 5,152,796 A | 10/1992 | Slamin | |
| 5,181,928 A | 1/1993 | Bolesky et al. | |
| 5,190,546 A | 3/1993 | Jervis | |
| 5,194,066 A | 3/1993 | Van Zile | |
| 5,197,720 A | 3/1993 | Renz et al. | |
| 5,201,882 A | 4/1993 | Paxson | |
| 5,286,260 A | 2/1994 | Bolesky et al. | |
| 5,314,479 A | 5/1994 | Rockwood, Jr. et al. | |
| 5,342,366 A | 8/1994 | Whiteside et al. | |
| 5,344,457 A | 9/1994 | Pilliar et al. | |
| 5,370,706 A | 12/1994 | Bolesky et al. | |
| 5,489,309 A | 2/1996 | Lackey et al. | |
| 5,489,311 A | 2/1996 | Cipolletti | |
| 5,507,817 A | 4/1996 | Craig et al. | |
| 5,507,826 A | 4/1996 | Besselink et al. | |
| 5,507,830 A | 4/1996 | DeMane et al. | |
| 5,549,706 A | 8/1996 | McCarthy | |
| 5,580,247 A | 12/1996 | Gittleman | |
| 5,584,695 A | 12/1996 | Lal Sachdeva et al. | |
| 5,597,378 A | 1/1997 | Jervis | |
| 5,607,431 A | 3/1997 | Dudasik et al. | |
| 5,609,645 A | 3/1997 | Vinciguerra | |
| 5,645,607 A | 7/1997 | Hickey | |
| 5,653,764 A | 8/1997 | Murphy | |
| 5,653,765 A | 8/1997 | McTighe et al. | |
| 5,658,349 A | 8/1997 | Brooks et al. | |
| 5,665,121 A | 9/1997 | Gie et al. | |
| 5,683,404 A | 11/1997 | Johnson | |
| 5,702,480 A | 12/1997 | Kropf et al. | |
| 5,702,486 A | 12/1997 | Craig et al. | |
| 5,725,592 A | 3/1998 | White et al. | |
| 5,755,720 A | 5/1998 | Mikhail | |
| 5,766,262 A | 6/1998 | Mikhail | |
| 5,766,263 A | 6/1998 | Grundei et al. | |
| 5,776,200 A | 7/1998 | Johnson et al. | |
| 5,782,921 A | 7/1998 | Colleran et al. | |
| 5,791,899 A | 8/1998 | Sachdeva et al. | |
| 5,858,020 A * | 1/1999 | Johnson et al. | 623/23.15 |
| 5,860,982 A | 1/1999 | Ro et al. | |
| 5,876,459 A | 3/1999 | Powell | |
| 5,885,295 A | 3/1999 | McDaniel et al. | |
| 5,888,206 A | 3/1999 | Lob et al. | |
| 5,888,208 A | 3/1999 | Ro | |
| 5,902,340 A | 5/1999 | White et al. | |
| 5,906,644 A | 5/1999 | Powell | |
| 5,931,871 A | 8/1999 | Baur et al. | |
| 5,944,756 A | 8/1999 | Fischetti et al. | |
| 5,954,725 A | 9/1999 | Sherman et al. | |
| 5,976,147 A | 11/1999 | LaSalle et al. | |
| 5,976,188 A | 11/1999 | Dextradeur et al. | |
| 6,048,365 A | 4/2000 | Burrows et al. | |
| 6,074,424 A | 6/2000 | Perrone, Jr. et al. | |
| 6,086,614 A | 7/2000 | Mumme | |
| 6,090,146 A | 7/2000 | Rozow, III et al. | |
| 6,099,570 A | 8/2000 | Livet et al. | |
| 6,102,956 A | 8/2000 | Kranz | |
| 6,109,602 A | 8/2000 | Schron, Jr. et al. | |
| 6,126,691 A | 10/2000 | Kasra et al. | |
| 6,136,035 A | 10/2000 | Lob et al. | |
| 6,139,584 A | 10/2000 | Ochoa et al. | |
| 6,165,223 A | 12/2000 | Metzger et al. | |
| 6,193,759 B1 | 2/2001 | Ro et al. | |
| 6,197,063 B1 | 3/2001 | Dews | |
| 6,203,575 B1 | 3/2001 | Farey | |
| 6,210,413 B1 | 4/2001 | Justis et al. | |
| 6,214,052 B1 | 4/2001 | Burkinshaw | |
| 6,214,053 B1 | 4/2001 | Ling et al. | |
| 6,257,593 B1 | 7/2001 | White | |
| 6,264,699 B1 * | 7/2001 | Noiles et al. | 623/23.23 |
| 6,273,915 B1 | 8/2001 | Grimes | |
| 6,290,726 B1 | 9/2001 | Pope et al. | |
| 6,299,648 B1 | 10/2001 | Doubler et al. | |
| 6,306,174 B1 | 10/2001 | Gie et al. | |
| 6,319,286 B1 | 11/2001 | Fernandez et al. | |
| 6,379,388 B1 | 4/2002 | Ensign et al. | |
| 6,682,568 B2 * | 1/2004 | Despres et al. | 623/22.42 |
| 6,692,530 B2 * | 2/2004 | Doubler et al. | 623/22.42 |
| 2002/0004685 A1 | 1/2002 | White | |
| 2002/0007220 A1 | 1/2002 | Gieret et al. | |
| 2002/0072802 A1 | 6/2002 | O'Neil et al. | |
| 2002/0103541 A1 | 8/2002 | Meyers et al. | |
| 2003/0204268 A1 * | 10/2003 | Gerbec et al. | 623/23.44 |

FOREIGN PATENT DOCUMENTS

| | | | |
|---|---|---|---|
| EP | 0 832 620 A3 | 4/1998 | |
| EP | 0832620 * | 4/1998 | A61F/2/30 |
| EP | 0 878 177 A3 | 11/1998 | |
| EP | 0 913 132 A1 | 5/1999 | |
| EP | 1 004 283 A2 | 5/2000 | |
| EP | 1 132 064 A2 | 9/2001 | |
| FR | 2 225 141 | 11/1974 | |
| FR | 2 705 558 | 12/1994 | |
| WO | WO 83/02555 | 8/1983 | |
| WO | WO 85/03426 | 8/1985 | |
| WO | WO 86/02260 | 4/1986 | |
| WO | WO 86/06954 | 12/1986 | |
| WO | WO 91/17723 | 11/1991 | |
| WO | WO 91/18563 | 12/1991 | |
| WO | WO 96/13233 | 5/1996 | |
| WO | WO 97/20525 | 6/1997 | |
| WO | WO 98/08467 | 3/1998 | |
| WO | WO 98/08468 | 3/1998 | |
| WO | WO 00/72784 A1 | 12/2000 | |
| WO | WO 02/07647 A2 | 1/2002 | |

* cited by examiner

MODULAR PROSTHESIS FOR REPLACING BONE AND METHOD

CROSS-REFERENCE TO RELATED APPLICATIONS

Not applicable.

BACKGROUND OF THE INVENTION

1. The Field of the Invention

The present invention relates to a modular prosthesis for replacing a portion of a bone having an articulating end and the methods of assembly and use thereof.

2. The Relevant Technology

Illustrated in FIG. 1 is a hip joint 10 by which a femur 12 rotatably couples with pelvic bone 14. Femur 12 comprises an articulating end 16, an elongated shaft 18, and a metaphyseal equivalent 20 which transitions therebetween. One occasion, it is necessary to replace the hip joint due to injury or other failure of the structure. Replacement of the hip joint typically comprises resecting articulating end 16 across metaphyseal equivalent 20 so as to expose the intramedullary canal extending through shaft 18. The distal end of a prosthesis is then inserted into the intramedullary canal of femur 12 so as to secure the prosthesis in place. Projecting from the prosthesis is a spherical head. The spherical head is configured to mate with a complimentary prosthetic or natural acetabulum or socket formed on pelvic bone 14.

In view of the fact that individuals come in all different sizes and shapes, it is often difficult to precisely fit and place the prosthesis for optimal function. Modular orthopedic prostheses have thus been provided which assist in optimizing fit and placement by allowing components of the prosthesis to be exchanged for different sizes and configurations. That is, by selecting independent modular components to construct a complete prosthesis, custom fitting of a patient's specific anatomy or specific bone condition can be accomplished.

Several attachment mechanisms are known in the art for connecting the components of a modular prosthesis. Generally, any two modular components are connected by one contiguous interface. Even three-piece modular connections typically rely on only one contiguous connection interface between any two modular components.

Because of the high physiological loads borne by the skeletal structure, orthopedic prostheses are subject to high bending, shear, and torsional loads. Where a single contiguous connection is used to connect components of a modular prosthesis, the applied loads can be localized, thereby increasing the failure at that point. It would therefore be an improvement in the art to provide modular orthopedic prostheses that can better withstand the mechanical service loads by better distributing the loads acting upon the prosthesis.

Furthermore, one of the advantages of modular orthopedic prostheses is the capacity to select, at the time of surgery, a desired orientation between modular components. Many modular connections known in the art do not facilitate a state of partial assembly that closely replicates the final longitudinal configuration of the prosthesis, where, in the state of partial assembly, the modular components can be freely rotated with respect to each other. It would therefore be another improvement in the art to provide modular prostheses that would accommodate a state of partial assembly that closely replicates the longitudinal configuration of the prosthesis while permitting free relative rotation between the modular components.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 2:
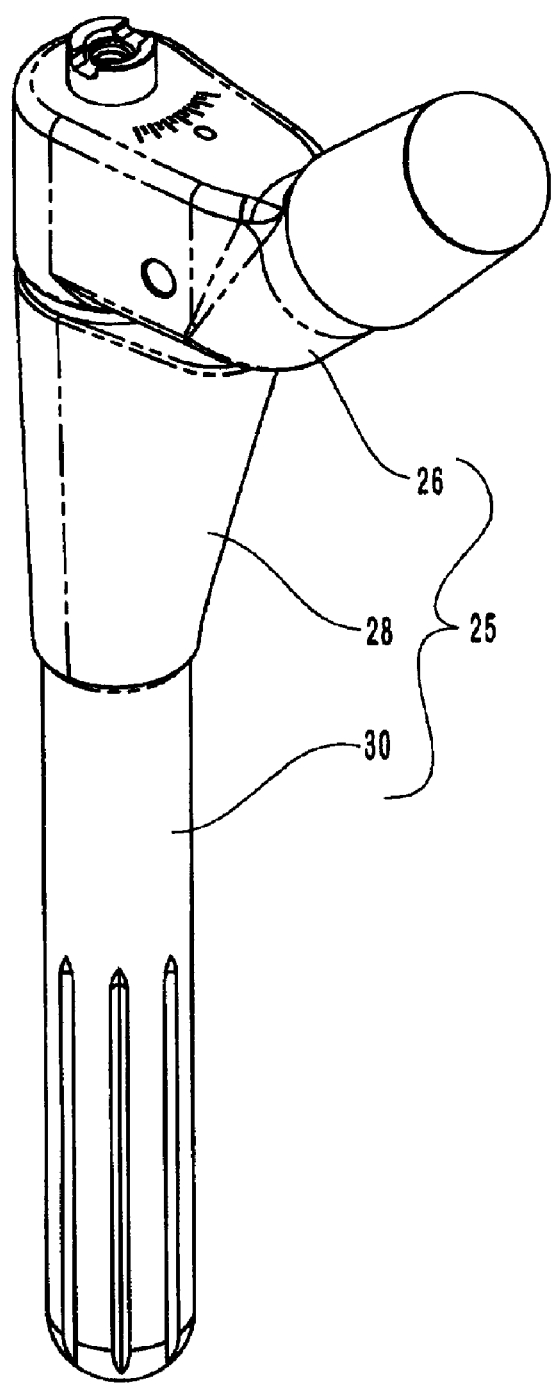
FIG. 2 is a perspective view of one embodiment of a modular prosthesis.
Figure 3:
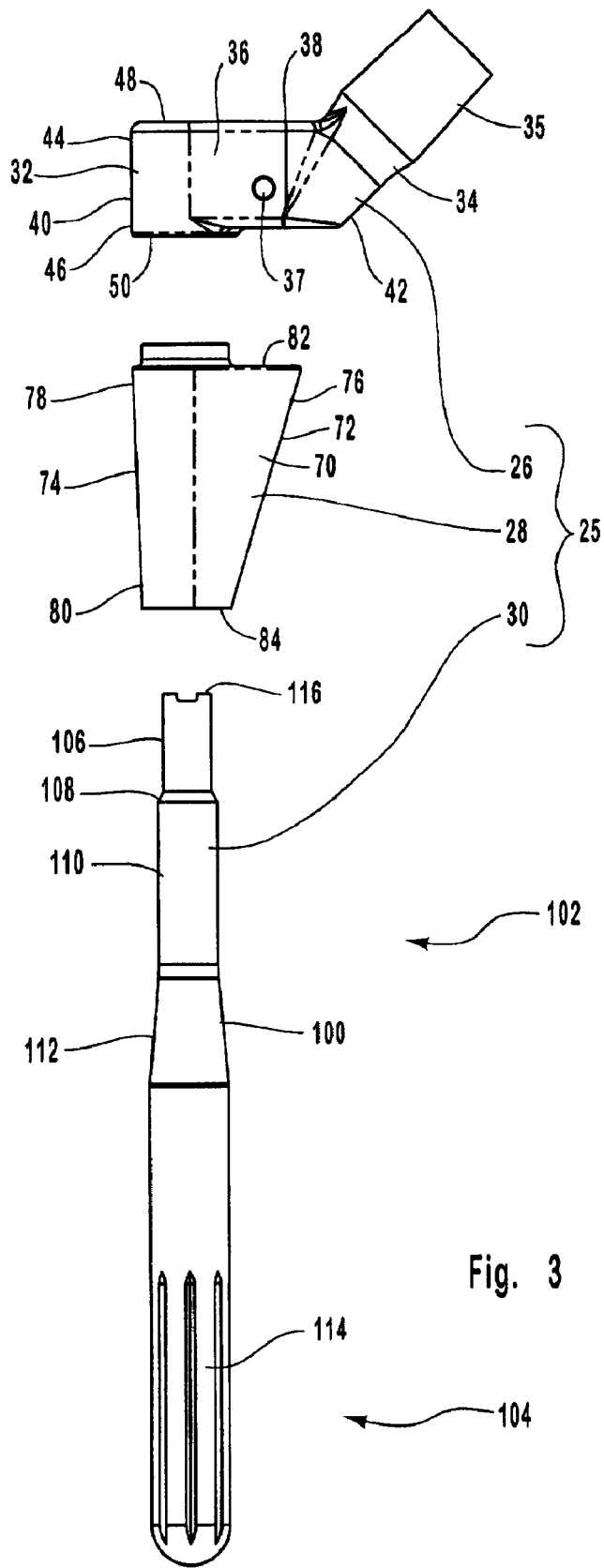
FIG. 3 is an exploded view of the modular prosthesis shown in FIG. 2.

Depicted in FIG. 2 is one embodiment of a modular prosthesis 25 incorporating features of the present invention. Modular prosthesis 25 is used for replacing a bone having an articulating end, a shaft, and a metaphyseal equivalent extending therebetween. Such bone can comprise the proximal portion of femur 12 as previously discussed, or the bone can comprise other bone portions, such as the distal femur, proximal tibia, or proximal humerus. As depicted in FIGS. 2 and 3, modular prosthesis 25 comprises a neck 26, a body 28, and a stem 30.

Neck 26 comprises a base 32 having a substantially elongated box shaped configuration with a post 34 projecting therefrom. Specifically, base 32 has a front face 36 and a back face 38 which each extend between a first side 40 and an opposing second side 42. Faces 36 and 38 and sides 40 and 42 each extend between a proximal end 44 and a distal end 46. Proximal end 46 terminates at a proximal end face 48 while distal end 46 terminates at a distal end face 50. A passageway 37 extends through base 32 between front face 36 and back face 38. Passageway 37 is configured to receive a pin or other structure so that neck 26 can be firmly connected to for separation of neck 26 and/or removal of modular prosthesis 25.

Post 34 is integral with base 32 and projects from second side 42 thereof at a desired angle. Post 34 terminates at a frustoconical surface 35 on which a spherical head (not shown) is selectively attached. The spherical head is adapted to articulate with a prosthetic or natural acetabulum (not shown).

Figure 4:
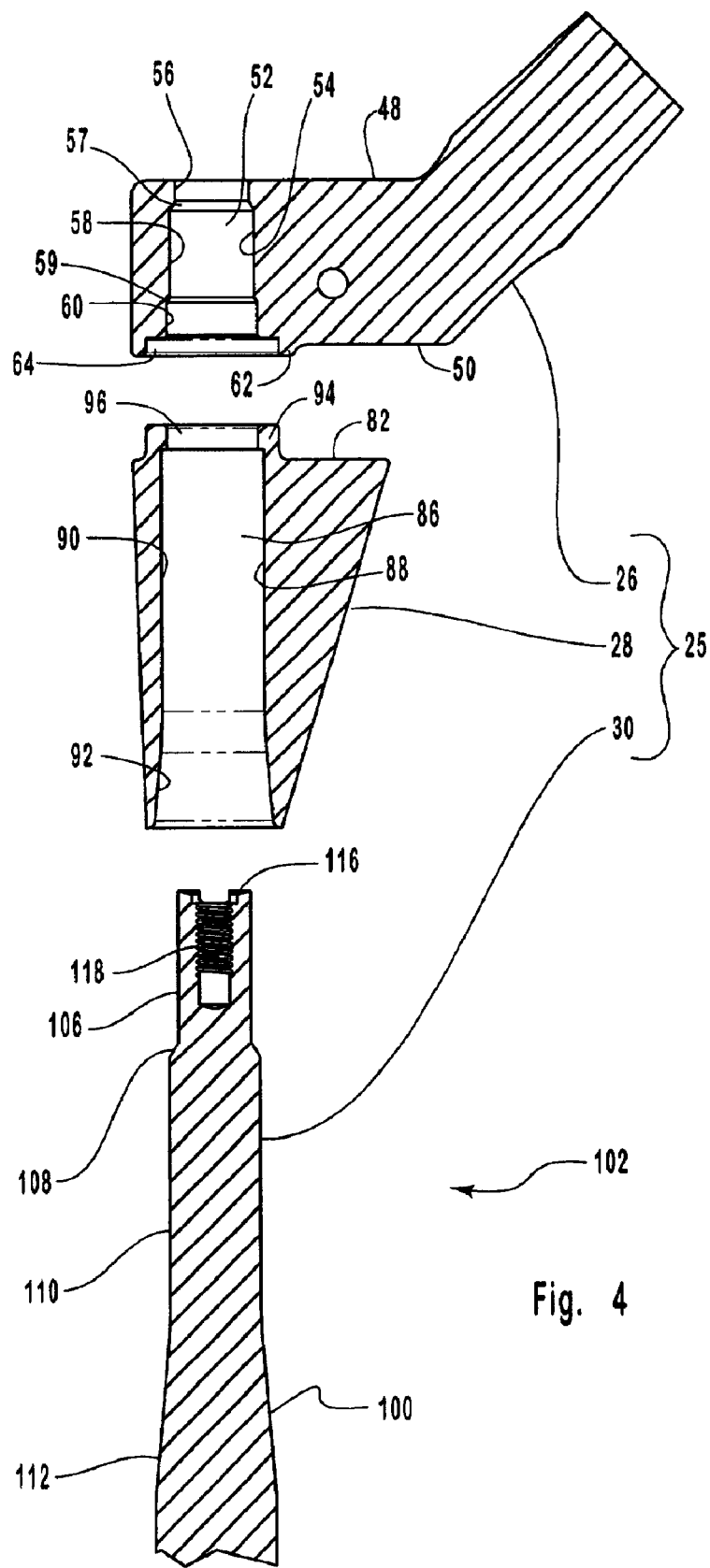
FIG. 4 is a cross sectional side view of the modular prosthesis shown in FIG. 3.

As depicted in FIG. 4, extending between opposing end faces 48 and 50 is a bore 52 bounded by an interior surface 54. Starting from proximal end face 48, interior surface 54 comprises a cylindrical proximal boundary wall 56, an outwardly sloping frustoconical shoulder 57, a cylindrical central boundary wall 58, an outwardly sloping frustoconical shoulder 59, and a cylindrical distal boundary wall 60. Boundary walls 56, 58, and 60 are concentrically disposed with each having an increasing larger maximum diameter, respectively.

An annular first rim 62 downwardly projects from distal end face 50 so as to encircle first bore 52. Annular first rim 62 bounds an opening 64 which is concentrically aligned with first bore 52 and has a larger diameter than boundary wall 60.

Returning to FIG. 3, body 28 has a front face 70 and an opposing back face 72 which each have an asymmetrical truncated wedge shape configuration. That is, each of the faces 70 and 72 extend between a first side face 74 and an opposing second side face 76. First side 74 slopes outward relative to a vertical axis at a first angle while second side 72 slopes outward at a second angle that is greater than the first angle. The angle of slope for sides 74 and 76 can vary depending on the intended use. Faces 70 and 72 and sides 74 and 76 each extend between a proximal end 78 and an opposing distal end 80. Proximal end 78 terminates at a proximal end face 82 while distal end 80 terminates at a distal end face 84.

Turning to FIG. 4, extending between end faces 82 and 84 is a bore 86 bounded by an interior surface 88. Interior surface 88 comprises a cylindrical proximal inner wall 90 and a frustoconical distal inner wall 92. Upwardly projecting from proximal end face 82 of body 28 is an annular second rim 94. Second rim 94 has an opening 96 extending therethrough in concentric alignment with bore 86. Opening 96 has an inside diameter smaller than the inside diameter of inner wall 90. As such, a flat shoulder 97 is formed therebetween. Furthermore, as will be discussed below, the outer diameter of second rim 94 is slightly larger than the inner diameter of first rim 62 so that a press fit connection can be formed therebetween.

Returning to FIG. 3, stem 30 has an exterior surface 100 that extends between a proximal end 102 and an opposing distal end 104. Proximal end 102 terminates at a proximal end face 116. A threaded socket 118 (FIG. 4) is recessed in proximal end 116. In general, and starting from proximal end face 116, proximal end 102 of stem 30 comprises a cylindrical proximal stem segment 106, a outwardly sloping frustoconical shoulder 108, a cylindrical central stem segment 110, and an outwardly sloping distal stem segment 112. Longitudinally recessed into distal end 104 of stem 30 are a plurality of radially spaced apart engagement grooves 114. Although stem 30 is shown as being linear, in alternative embodiments stem 30 or portions there can be curved. Stem 30 can also come in different lengths.

Figure 5:
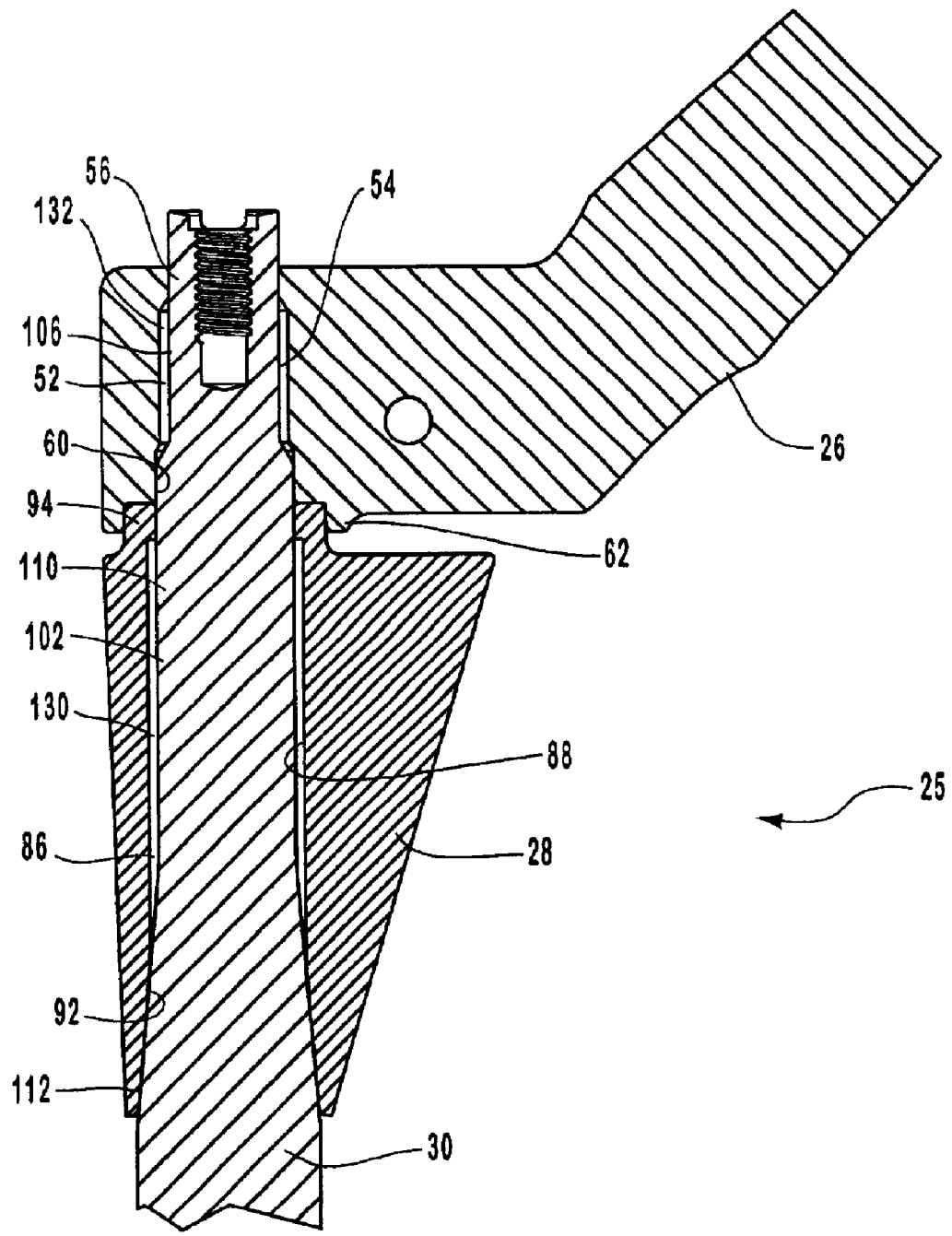
FIG. 5 is a cross section side view of the modular prosthesis shown in FIG. 4 in an assembled state.

As depicted in FIGS. 4 and 5, to assemble modular prosthesis 25, proximal end 102 of stem 30 is received within bore 86 of body 28. Body 28 is advanced over stem 30 until distal inside wall 92 of body 28 seats against stem segment 112. In this embodiment, opening 96 bounded by second rim 94 on body 28 has an inside diameter that is the same as or slightly larger than the outside diameter of central stem portion 110. As such, body 28 can be manually advanced over stem 30 to facilitate the seating of inside wall 92 against stem segment 112. One of the benefits of this configuration is that body 28 can first be positioned over stem 30 with a slight space between the seated engagement and then selectively rotated relative to stem 30 to obtain a desired orientation. Once selectively oriented, body 30 can be seated on stem 30.

Inside wall 92 and stem segment 112 each have a complementary frustoconical configuration so as to form a releasable self-locking taper connection therebetween. As used in the specification and appended claims, the term "self-locking taper connection" is intended to include complimentary frustoconical surfaces that when seated together under compression preclude rotation relative to each other but which permit selective separation under tension. In general, self-locking taper connections are formed when each of the complementary frustoconical surfaces has an included angle in a range between about 2° to about 8° with about 3° to about 6° being more common. In other embodiments, other angle ranges can also be used.

Next, proximal end 102 of stem 30 is received within bore 52 of neck 26. Proximal boundary wall 56 and distal boundary wall 60 of neck 26 each have an inner diameter that is slightly smaller than the outer diameter of proximal stem segment 106 and central stem segment 110, respectively. However, because the inner diameter of distal boundary wall 60 of neck 26 is larger than the outer diameter of proximal stem segment 106, neck 26 can be freely advanced over a portion of stem 30. In this partially assembled state, neck 26 can be freely rotated on stem 30, thereby permitting easy adjustment of neck 26 in its close to final state.

Once neck 26 is positioned in it desired orientation, neck 26 is pressed onto stem 30. Specifically, neck 26 is further advanced over stem 30 so that a releasable press fit connection is formed between proximal boundary wall 56 and proximal stem segment 106 and between distal boundary wall 60 and central stem segment 110. To enable releasable press fit connections, the amount of interference between the engaging surfaces is typically less than the radial yield strain of the chosen material, and preferably less than 75% of the radial yield strain. To ensure that a press fit is achieved, however, the interference between the engaging surfaces is typically at least 10% of the radial yield strain and preferably greater than 25% of the radial yield strain. For example, provided that the proximal stem portion 106 defines a diameter of 0.500 inch, and provided that stem 30 and neck 26 are made from titanium alloy with 6% vanadium and 4% aluminum, then in one embodiment the yield strain would be approximately 0.0035 inch. Therefore, one example of interference would be greater than 0.0009 inch and less than 0.0027 inch.

As neck 26 is press fit onto stem 30, first rim 62 projecting from neck 26 passes around second rim 94 projecting from body 28 so as to form a releasable press fit connection therebetween. This press fit connection not only produces a rigid engagement between neck 26 and base 28, but it also radially inwardly biases second rim 94 against exterior surface 100 of stem 30 so as to form a secure frictional engagement therebetween. In alternative embodiments, it is appreciated that rims 62 and 94 can be switched between neck 26 and base 28. Furthermore, rims 62 and 64 need not form a continuous loop, but can comprise two or more segments of a loop.

In the fully assembled state of modular prosthesis 25 as illustrated in FIG. 5, a cylindrical gap 130 is formed between exterior surface 100 of shaft 30 and interior surface 88 of body 28. Gap 130 extends from the self-locking taper connection at the distal end of body 26 to the frictional engagement connection between second rim 94 and shaft 30 at the proximal end of body 26. Similarly, a cylindrical gap 132 is formed between exterior surface 100 of shaft 30 and interior surface 54 of neck 26. Gap 132 extends between the press fit connections formed on the opposing ends of neck 26.

By separating the releasable connections with gaps, such as gaps 130 and 132, reaction forces and stresses associated with the connections are decreased when bending loads act upon modular prosthesis 25. Decreased reaction forces and stresses provide for higher performance assemblies that can carry higher bending loads and reduce fretting or fatigue caused by cyclic loads. Furthermore, the higher performance assembly can enable smaller sizes that sufficiently withstand physiological loads.

In one embodiment, the distance between the releasable connections is generally greater than the sum of the connection lengths. The "connection length" is simply the length over which two surface engage to form the connection. Preferably, though not required, the distance between the releasable connections is at least greater than the shortest of the spaced apart connection lengths. By way of example and not by limitation, the distance between spaced apart connections or the length of the gap between connections is typically in a range between about 10 mm to about 50 mm or about 5 mm to about 25 mm. In other embodiments, the length of the gap can simply be greater than about 5 mm, 10 mm, or 15 mm, although shorter distances can also be used. Although each "connection length" can be any desired length, on one embodiment each connection length is in a range between about 0.5 mm to about 15 mm, or about 1 mm to about 10 mm, or about 1 mm to about 5 mm. In alternative embodiments, it is appreciated that the gap need not completely encircle shaft 30. Furthermore, the gap need not extend fully between spaced apart connections.

Figure 6:
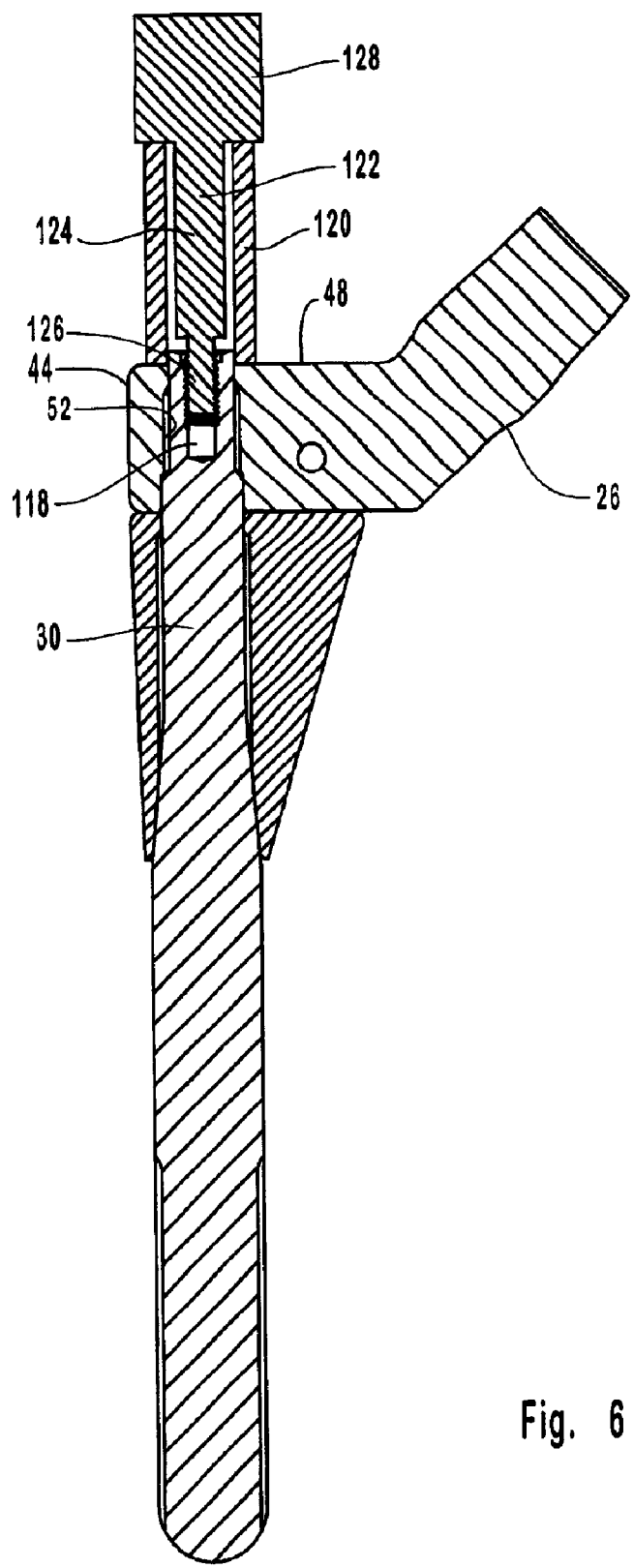
FIG. 6 is a cross section side view of a mounting assembly used in the assembly of the modular prosthesis.

A variety of alternative mechanisms can be used to press fit neck 26 onto shaft 30. In one embodiment as depicted in FIG. 6, a tubular sleeve 120 is provided. Sleeve 120 has an inner diameter that is slightly larger than the diameter of bore 52 at proximal end 44 of neck 26. The distal end of sleeve 120 is positioned on proximal end face 48 of neck 26 so as to encircle bore 52. Next, a drive bolt 122 is provided. Drive bolt 122 comprises an elongated shaft 124 that is received within sleeve 130, a threaded end 126 that is threaded into socket 118 of stem 30, and an enlarged head 128 which outwardly projects from shaft 124 so as to rest on the proximal end of sleeve 120. Accordingly, by screwing drive bolt 122 into socket 118, head 128 on drive bolt 122 drives sleeve 120 downward, which in turn drives neck 26 onto stem 30.

In one alternative to the previously discussed embodiment of modular prosthesis 25, second rim 94 has an inner diameter that is slightly smaller than central stem segment 110 of stem 30. As a result, second rim 94 must be press fit onto central stem segment 110. This press fit connection can be accomplished by transferring the required force through neck 26. Alternatively, prior to attaching neck 26 onto stem 30, an elongated sleeve 120 can be passed over the proximal end of stem 30 so as to rest against proximal end face 82 and/or annular rim 94. Drive bolt 122 is then be used to press fit body 28 onto stem 30. Once positioned, sleeve 120 and drive bolt 122 are removed for the attachment of neck 26.

The components of modular prosthesis 25 may be made from any suitable biocompatible material that can withstand the physiological loads during the lifetime of the implant. Preferentially, the components of modular prosthesis 25 are made from biocompatible metals, such as titanium alloys, zirconium alloys, cobalt chromium alloys, stainless steels or combinations thereof. It is appreciated that the various components come in a variety of different sizes and configurations so that modular prosthesis 25 can be tailored to precisely fit its intended use.

Depicted in the remaining FIGS. 7–22 are alternative embodiments of modular prosthesis wherein different combinations and configurations of releasable press fit connections and releasable self-locking tapered connections are used to secure neck 26 and base 28 to stem 30. Like elements between the various embodiments are identified by like reference characters.

Figure 7:
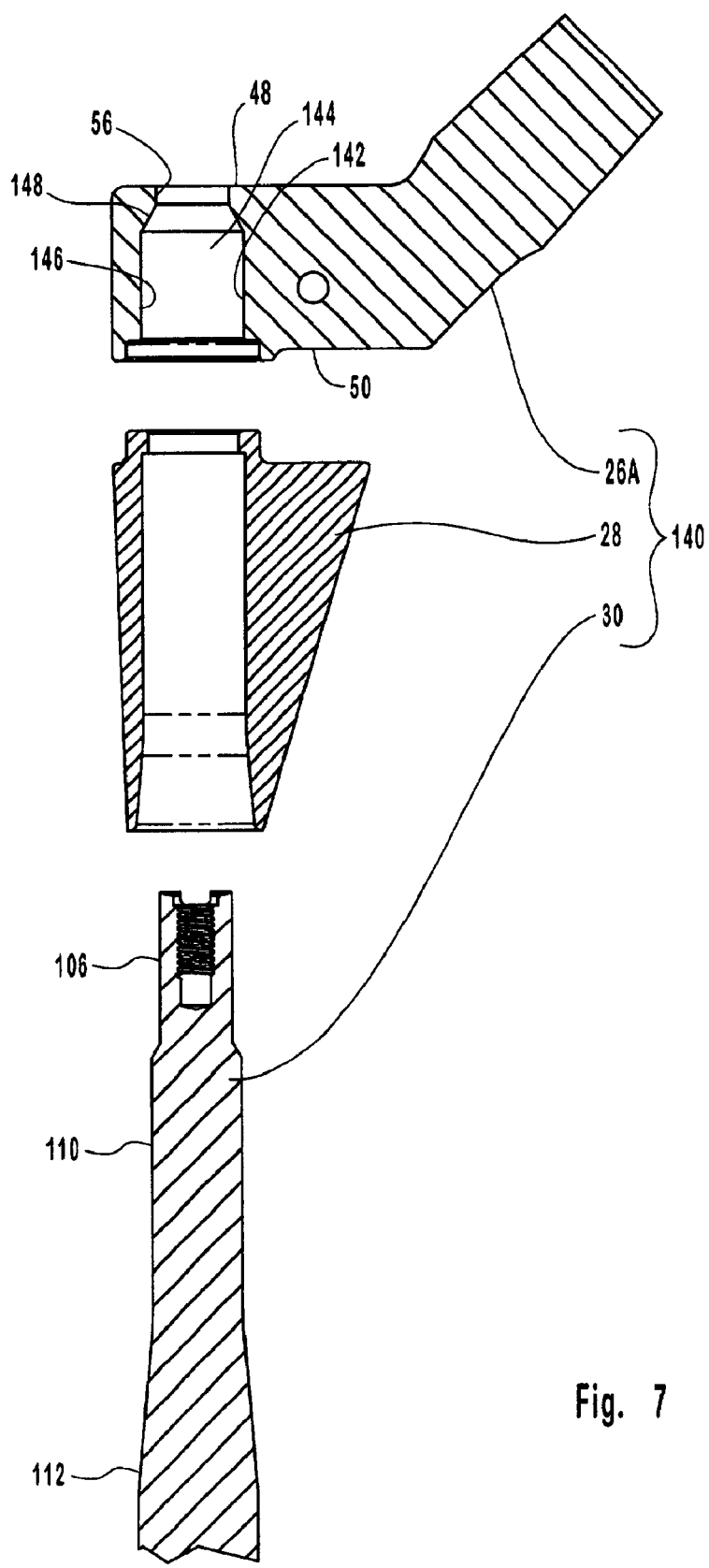
FIG. 7 is a exploded cross section side view of an alternative embodiment of a modular prosthesis where the distal end of the neck does not directly frictionally engage with the stem.
Figure 8:
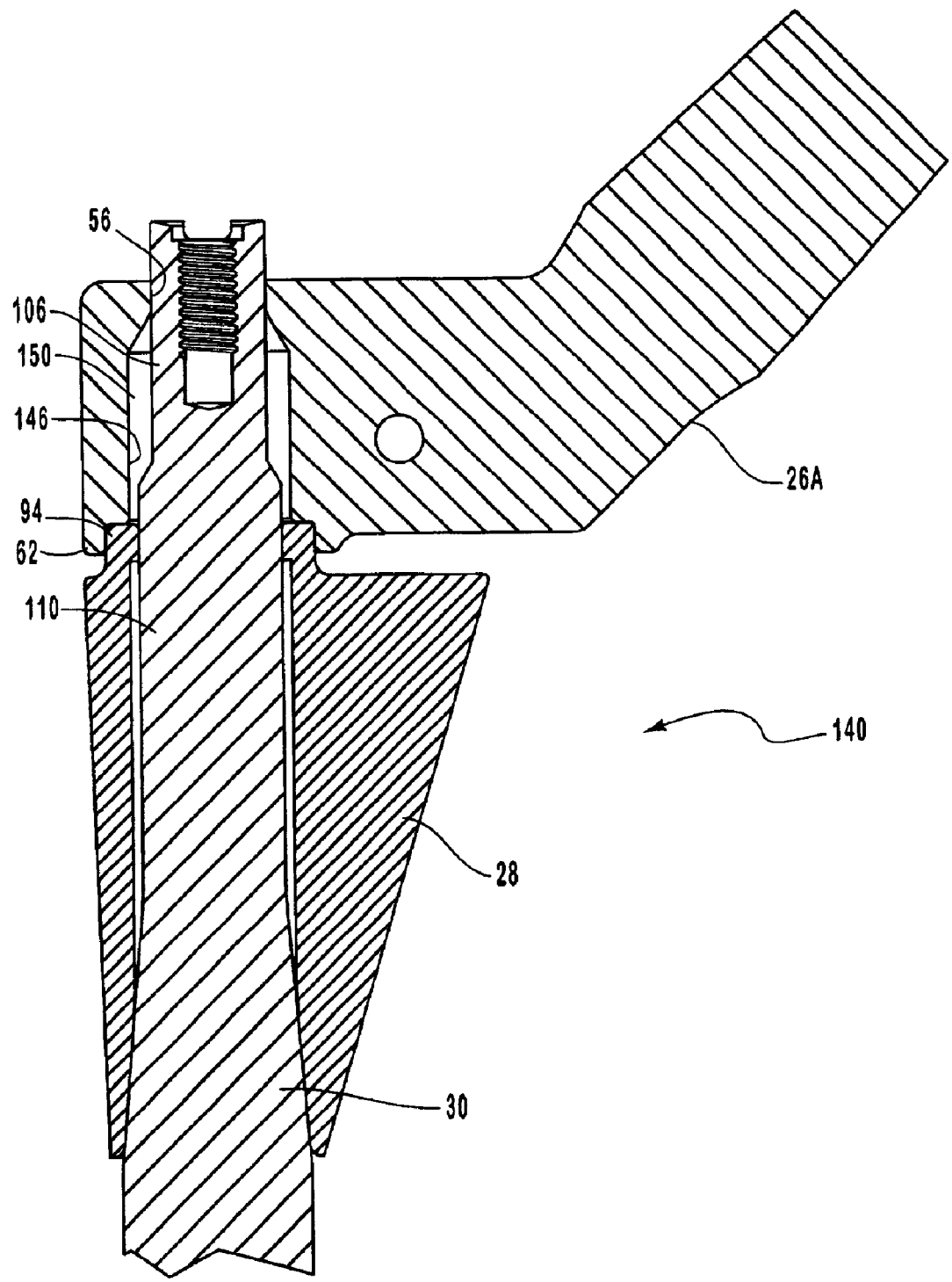
FIG. 8 is a cross sectional side view of the modular prosthesis shown in FIG. 7 in an assembled state.

Depicted in FIGS. 7 and 8 is an alternative embodiment of a modular prosthesis 140. Modular prosthesis 25 and 140 are substantially identical except for neck 26. As previously discussed, the distal end of neck 26 of modular prosthesis 25 is configured to produce a direct press fit connection with both body 28 and stem 30. In contrast, the distal end of a neck 26A of modular prosthesis 140 is configured only to produce a press fit connection with body 28.

Specifically, neck 26A has an interior surface 142 that bounds a bore 144 extending between proximal end face 48 and distal end face 50. Interior surface 142 comprises cylindrical proximal boundary wall 56 and a cylindrical distal boundary wall 146 with a tapered shoulder 148 extending therebetween. As depicted in FIG. 8, distal boundary wall 146 has an inner diameter larger than central stem segment 110 of stem 30. As such, distal boundary wall 146 of stem 26A does not produce a direct press fit connection with stem 30 when mounted thereon. Stem 26A is secured to stem 30, however, through the press fit connection between proximal boundary wall 56 of neck 26A and proximal stem segment 106 of stem 30 and through the press fit connection between rims 62 and 94, as previously discussed. A substantially cylindrical gap 150 extends between the spaced apart press fit connections. Body 28 is again mounted to stem 30 as previously discussed with regard to modular prosthesis 25.

Figure 9:
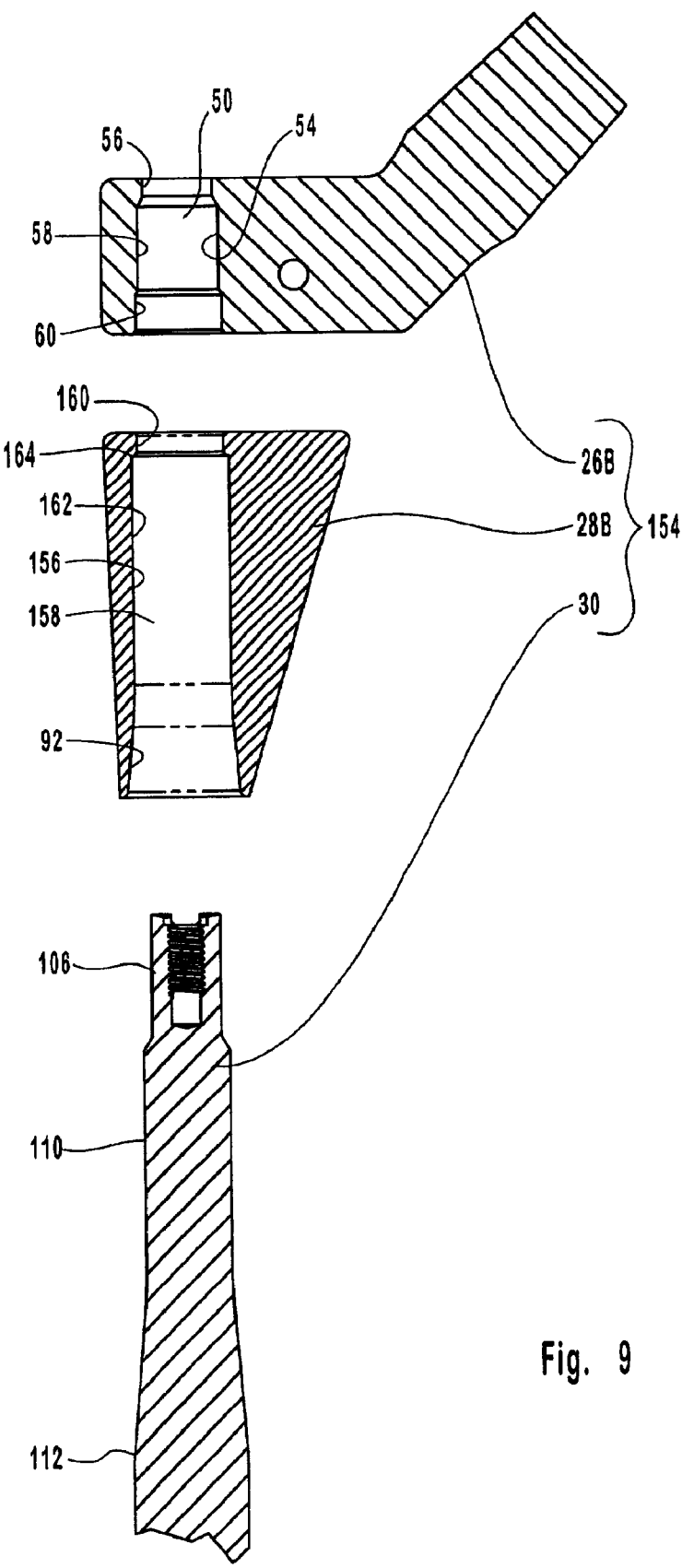
FIG. 9 is an exploded cross sectional side view of an alternative embodiment of a modular prosthesis wherein the neck and body thereof do not couple together.
Figure 10:
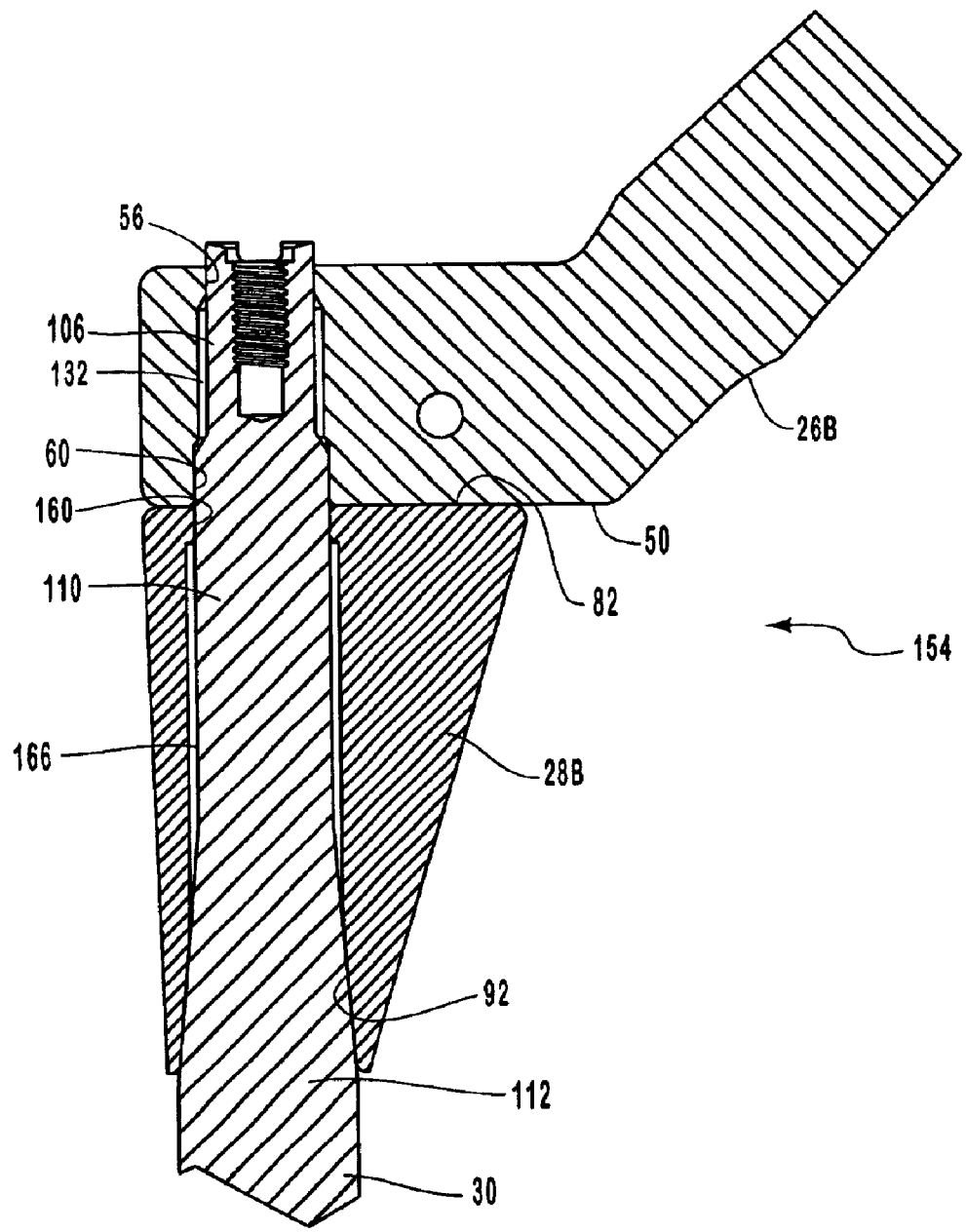
FIG. 10 is a cross sectional side view of the modular prosthesis shown in FIG. 9 in an assembled state.

Depicted in FIGS. 9 and 10 is an alternative modular prosthesis 154. Modular prosthesis 154 comprises a neck 26B, a base 28B and stem 30. Neck 26B is substantially identical to neck 26 in FIGS. 3–5 except that annular rim 62 and corresponding opening 64 have been removed. As such, interior surface 54 of bore 52 comprises proximal boundary wall 56, central boundary wall 58, and distal boundary wall 60, as previously discussed.

Body 28B is similar to body 28 in FIGS. 3–5 except that annular rim 94 has been removed therefrom. Body 28B has an interior surface 156 that bounds a bore 158 extending therethrough. Interior surface 156 comprises a cylindrical proximal inner wall 160 and a cylindrical central inner wall 162 positioned distal thereof. Proximal inner wall 160 has an inner diameter smaller than central inner wall 162 such that a shoulder 164 is formed therebetween. Located distal of central inner wall 162 is frustoconical distal inner wall 92.

As depicted in FIG. 10, body 28B is received over stem 30 such that a self-locking tapered connection is formed between frustoconical distal inner wall 92 of body 28B and frustoconical distal stem segment 112 of stem 30. Furthermore, proximal inner wall 160 of body 28B forms a press fit connection with central stem segment 110 of stem 30. A substantially cylindrical gap 166 extends between the self-locking taper connection and the press fit connection.

As previously discussed with modular prosthesis 25, proximal boundary wall 56 and distal boundary wall 60 of neck 26B are in a press fit connection with proximal stem segment 106 and central stem segment 110 of stem 30, respectively. These press fit connections are separated by annular gap 132.

In the embodiment depicted, distal end face 50 of neck 26B is biased against proximal end face 82 of body 28B. Depending on the desired position for neck 26B, neck 26B can be longitudinally spaced apart from body 28B while maintaining the two spaced apart press fit connections with stem 30. Furthermore, as with all other embodiments, at the time of attachment neck 26B can be secured at any desired orientation relative to body 28B.

Figure 11:
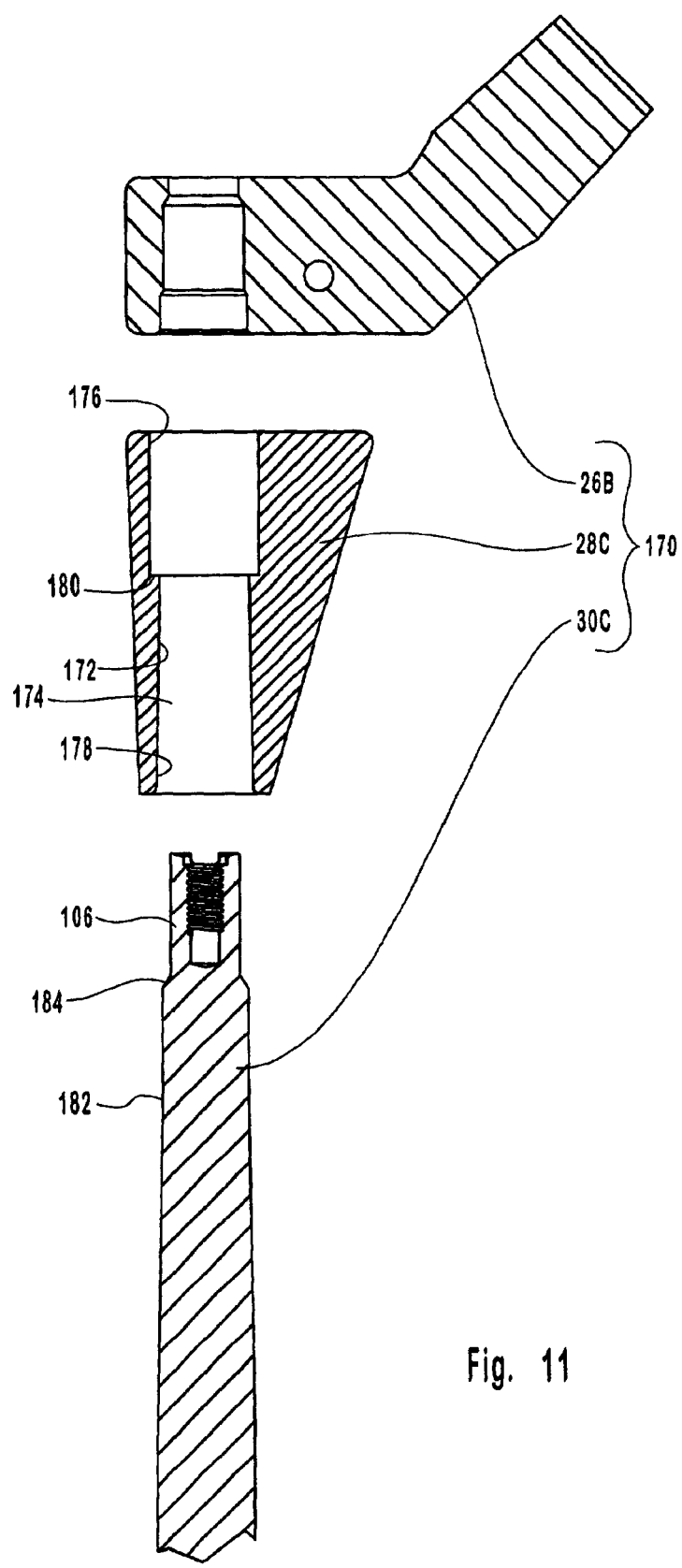
FIG. 11 is an exploded cross section side view of an alternative embodiment of a modular prosthesis wherein the body thereof engages with the stem in a single self-locking taper connection.

Depicted in FIG. 11 is yet another alternative embodiment of a modular prosthesis 170. Modular prosthesis 170 comprises neck 26B as previously discussed, a body 28C, and a stem 30C. Body 28C comprises an interior surface 172 bounding a bore 174 extending therethrough. Interior surface 172 comprises a cylindrical proximal inner wall 176 and a frustoconical distal inner wall 178. Proximal inner wall 176 has a diameter larger than the diameter of distal inner wall 178 at the intersection thereof. As such, a flat shoulder 180 is formed therebetween.

Figure 12:
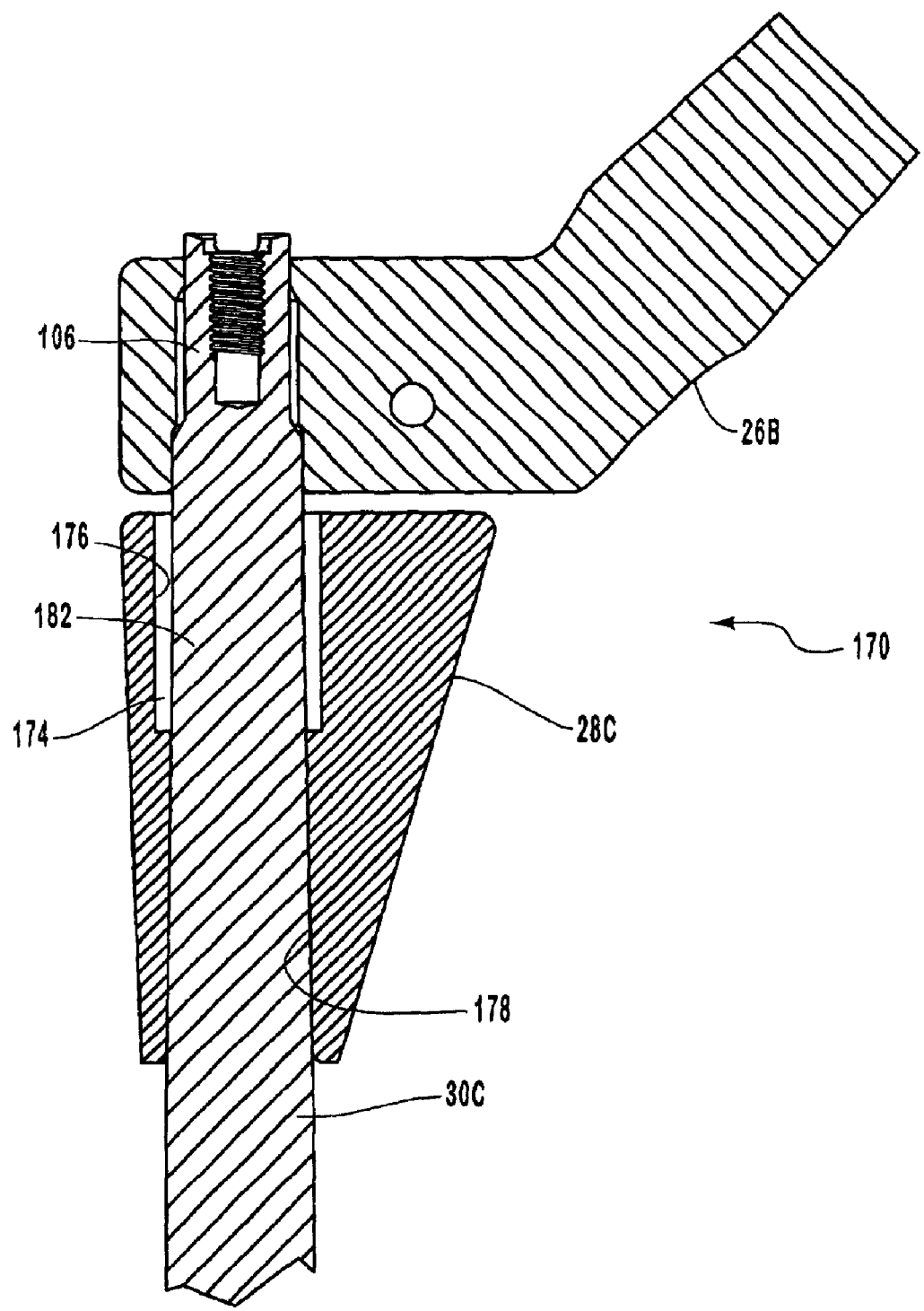
FIG. 12 is a cross sectional side view of the modular prosthesis shown in FIG. 11 in an assembled state.

The proximal end of stem 30C comprises cylindrical proximal stem segment 106 and a frustoconical distal stem segment 182 positioned distally therefrom. An outwardly sloping shoulder 184 is formed therebetween. As depicted in FIG. 12, stem 30C is configured to be received within bore 174 of body 28C so that a self-locking tapered connection is formed between frustoconical distal inner wall 178 of body 28C and frustoconical distal stem segment 182 of stem 30C. Proximal inner wall 176 of body 28C has an inner diameter larger than the outer diameter of distal stem segment 182 such that proximal inner wall 176 encircles stem 30C at a spaced offset. Neck 26A connects with stem 30C in the same way as previously discussed with regard to modular prosthesis 154.

Figure 13:
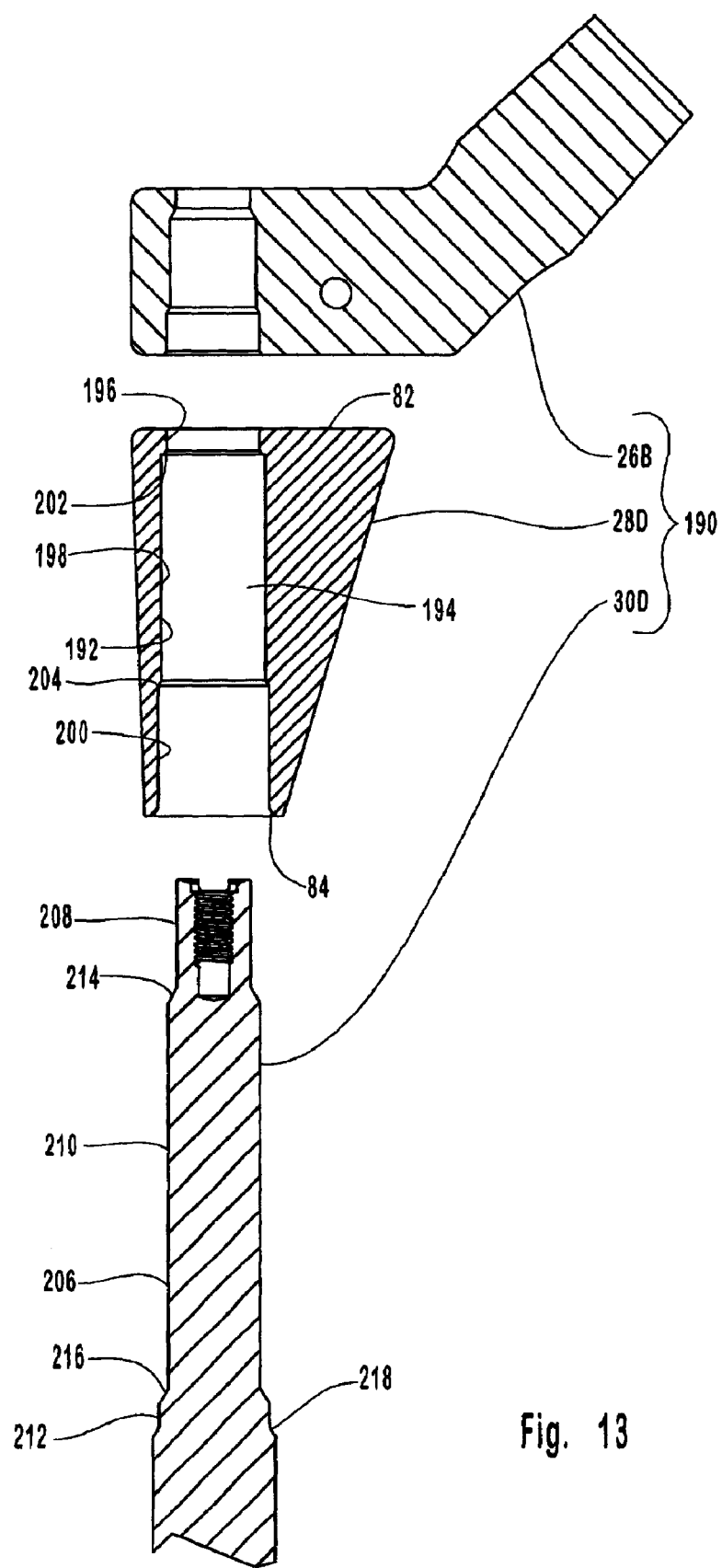
FIG. 13 is an exploded cross sectional side view of an alternative embodiment of a modular prosthesis wherein the distal end of the body thereof connects with the stem in a press fit connection.
Figure 14:
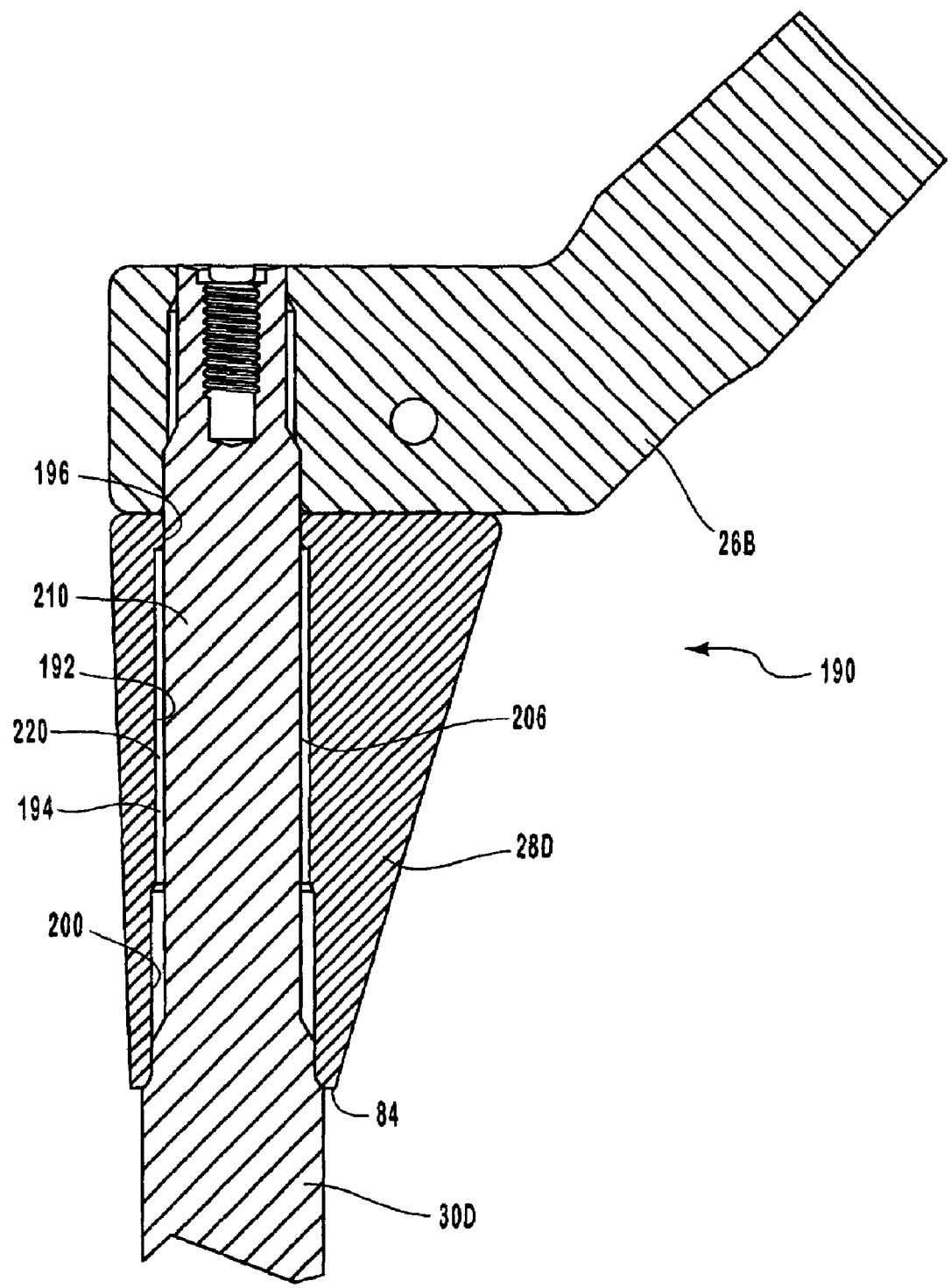
FIG. 14 is a cross section side view of the modular prosthesis shown in FIG. 13 in an assembled state.

Depicted in FIGS. 13 and 14 is another alternative embodiment of a modular prosthesis 190. Modular prosthesis 190 comprises neck 26B as previously discussed, a body 28D, and a stem 30D. Unlike the prior embodiments where the distal end of the body 28 coupled with stem 30 in a self-locking tapered connection, in this embodiment the distal end of body 28D couples with stem 30D in a press fit connection.

Specifically, body 28D has an interior surface 192 that bounds the bore 194 extending therethrough. Interior surface 192 comprises a cylindrical proximal inner wall 196, a cylindrical central inner wall 198, and a cylindrical distal inner wall 200. Each of inner walls 196, 198, and 200 of body 28D are concentrically disposed with increasing diameters extending from the proximal end to the distal end. As such, a first shoulder 202 extends between proximal inner wall 196 and central inner wall 198 while a second shoulder 204 extends between central inner wall 198 and distal inner wall 200.

Similarly, the proximal end of shaft 30D comprises a cylindrical proximal stem segment 208, a cylindrical central stem segment 210, and a cylindrical distal stem segment 212. Stem segments 208, 210, and 212 are also concentrically disposed each have a corresponding increased diameter. As such, a first shoulder 214 is disposed between stem segments 208 and 210 while a second shoulder 216 is formed between stem segments 210 and 212. A location shoulder 218 outwardly slopes from the distal end of distal stem segment 212.

As depicted in FIG. 14, stem 30D is received within bore 194 of body 28D such that proximal inner wall 196 and distal inner wall 200 of body 28 form a press fit connection with central stem segment 210 and distal stem segment 212 of stem 30D, respectively. Distal end face 84 of body 28D biases against location shoulder 218 to ensure proper placement of body 28D. That is, location shoulder 218 acts as a stop for body 28D. As with other embodiments, a substantially cylindrical gap 220 is formed between interior surface 192 of body 28D and exterior surface 206 of stem 30D and extends between the opposing press fit connections.

With further regard to modular prosthesis 190, neck 26B forms a press fit connection at the opposing proximal and distal ends thereof with stem 30D. These press fit connections are the same as previously discussed with regard to neck 26B.

Figure 15:
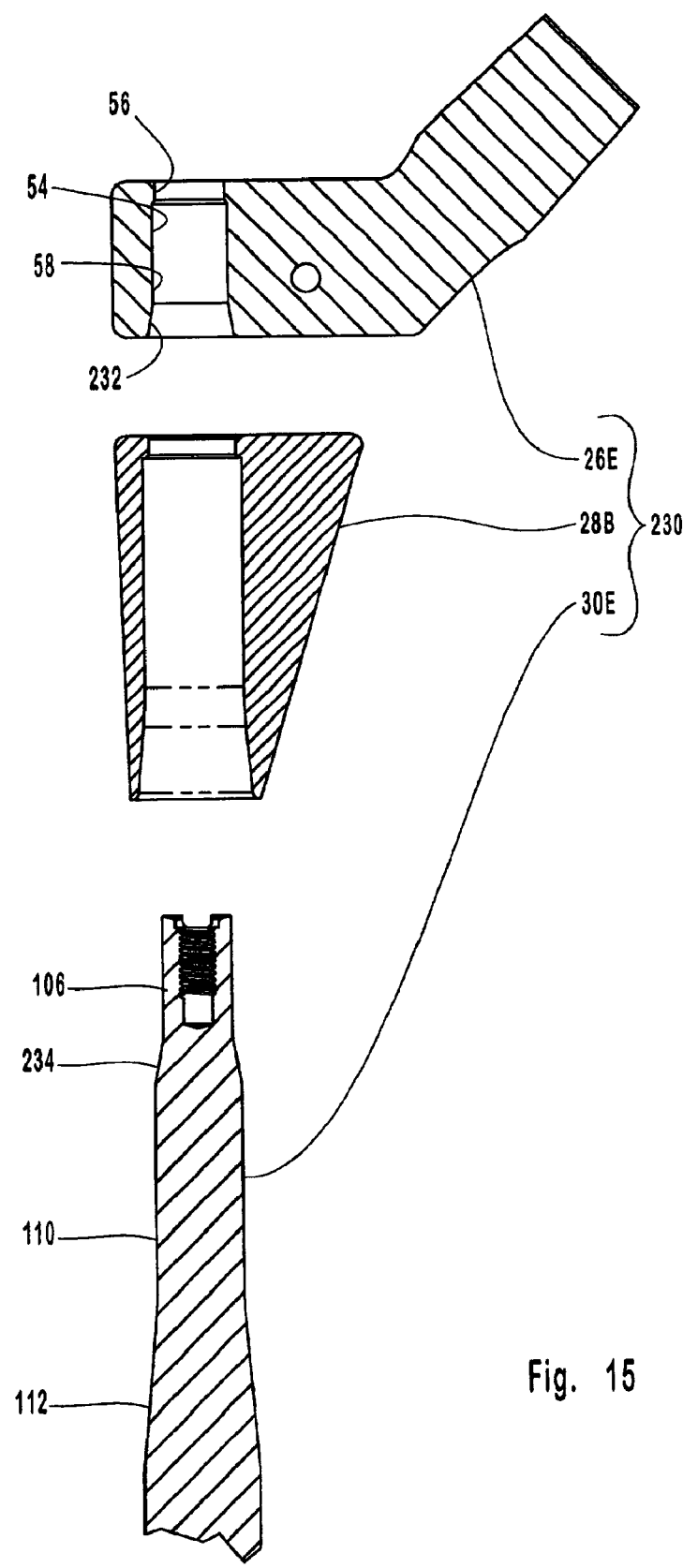
FIG. 15 is an exploded cross sectional side view of an alternative embodiment of a modular prosthesis wherein the distal end of the neck engages with the stem in a self-locking taper connection.
Figure 16:
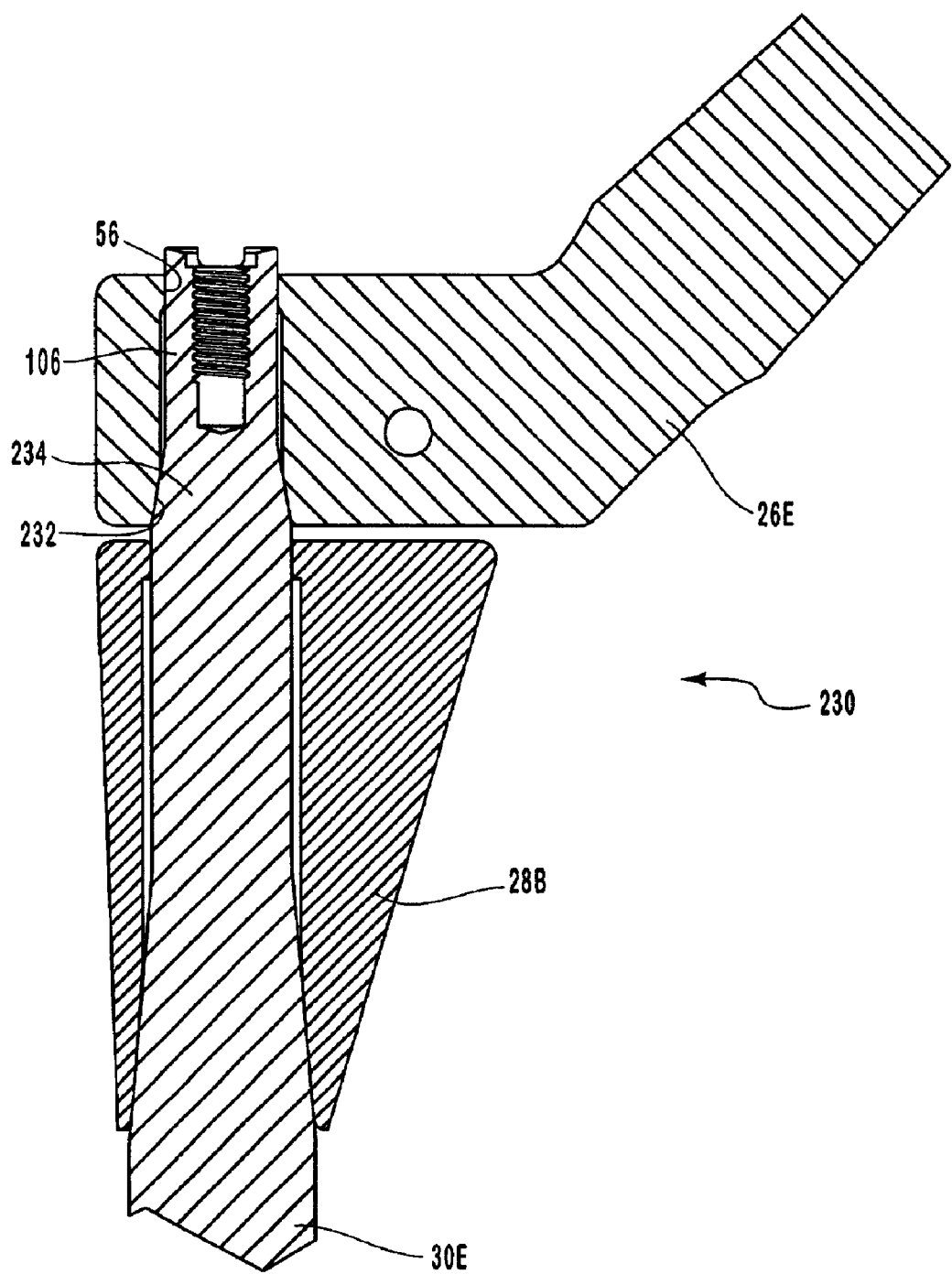
FIG. 16 is a cross sectional side view of the modular prosthesis shown in FIG. 15 in an assembled state.

Depicted in FIGS. 15 and 16, is still another alternative embodiment of a modular prosthesis 230. Modular prosthesis 230 comprises a stem 26E, body 28B as previously discussed with regard to FIGS. 9 and 10, and a stem 30E. Modular prosthesis 230 is similar to modular prosthesis 154. For example, neck 26E is similar to neck 26B except that cylindrical distal boundary wall 60 of neck 26B has been replaced with a frustoconical distal boundary wall 232.

Stem 30E has been modified so that a frustoconical stem segment 234 is formed between proximal stem segment 106 and central stem segment 110. As depicted in FIG. 16, body 28B is mounted on stem 30E in substantially the same way as previously discussed with regard to modular prosthesis 154. Neck 26E is mounted on stem 30E so that frustoconical distal boundary wall 232 of neck 26E mates in a self-locking taper connection with frustoconical stem segment 234 of stem 30E. Proximal boundary wall 56 of neck 26E mates in a press fit connection with proximal stem segment 106 of stem 30E.

Figure 17:
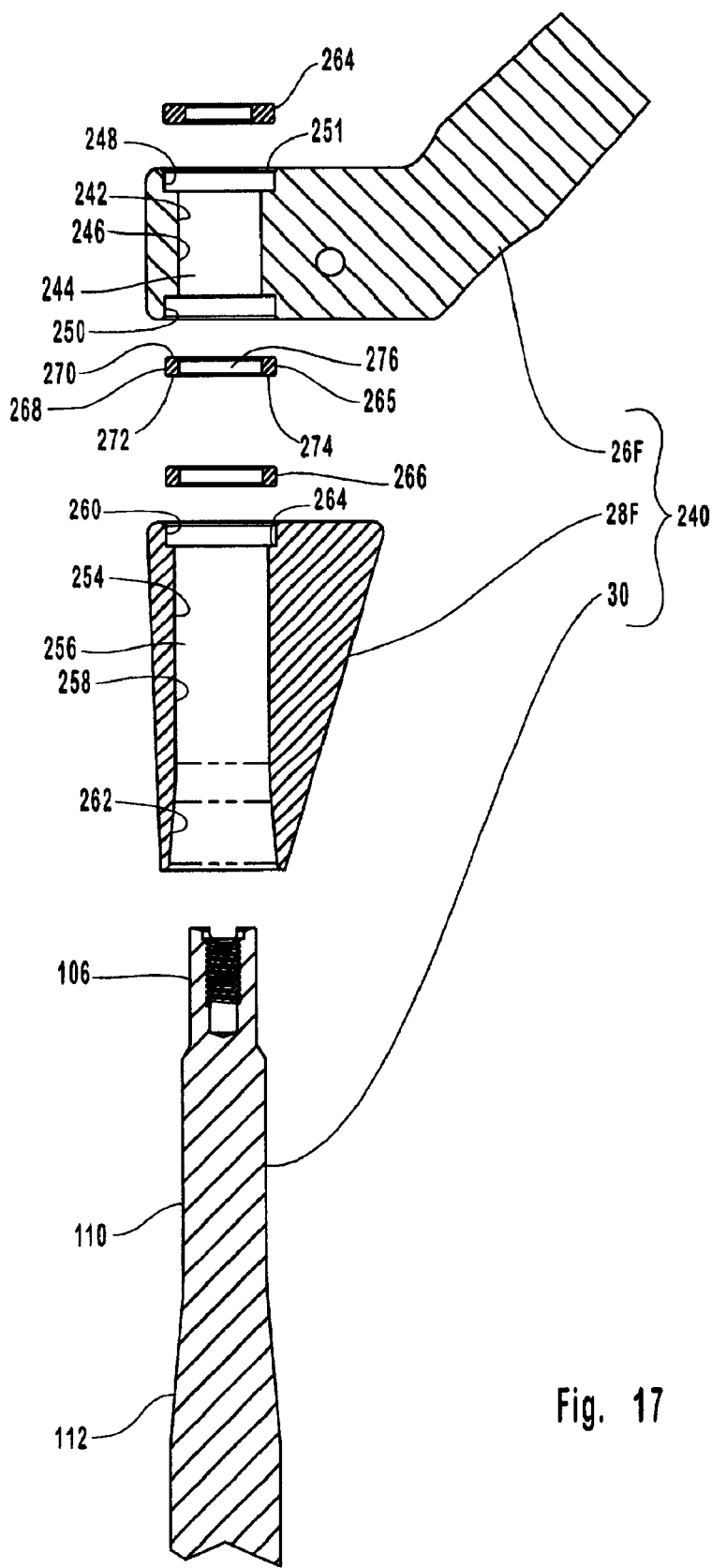
FIG. 17 is an exploded cross sectional side view of an alternative embodiment of a modular prosthesis wherein washers are used to indirectly press fit the neck and body to the stem.
Figure 18:
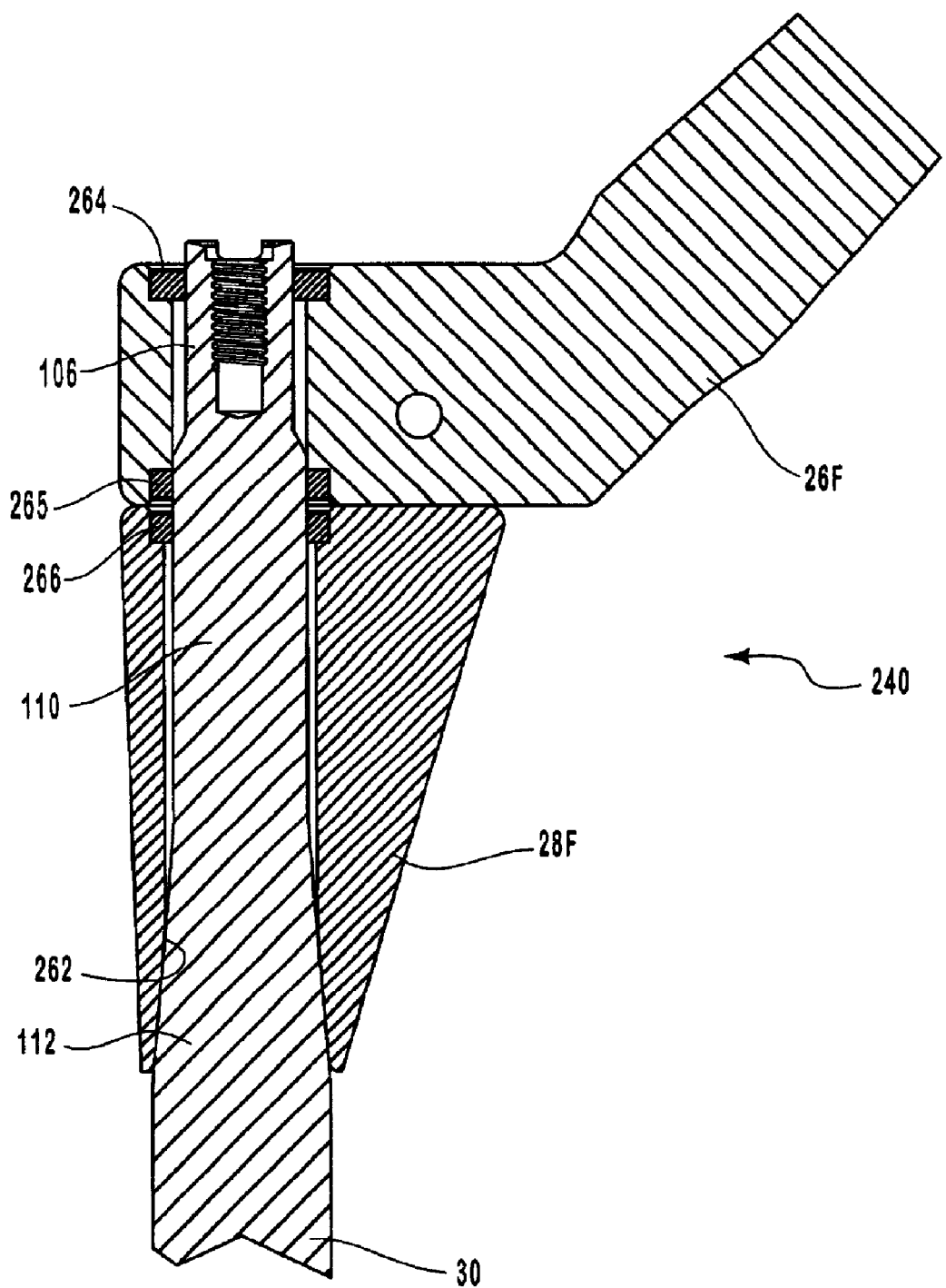
FIG. 18 is a cross sectional side view of the modular prosthesis shown in FIG. 17 in an assembled state.

Depicted in FIGS. 17 and 18 is a modular prosthesis 240. Modular prosthesis 240 comprises a neck 26F, a body 28F, and stem 30 as previously discussed. Modular prosthesis 240 is similar to modular prosthesis 154 depicted in FIGS. 9 and 10. The primary distinction is that unlike modular prosthesis 154 which uses direct press fit connections between neck 26B and stem 30 and also between the proximal end of body 28B and stem 30, washers are used in association with neck 26F and body 28F to facilitate an indirect press fit connection with stem 30.

Specifically, neck 26F has an interior surface 242 which bounds a bore 244 extending therethrough. Interior surface 242 comprises a cylindrical central boundary wall 246 with a proximal washer seat 248 formed proximal thereof and a distal washer seat 250 formed distal thereof. Washer seats 248 and 250 have substantially the same diameter which is larger than the inner diameter of central boundary wall 246. As such, an annular shoulder 251 extends between each washer seat 248, 250 and central boundary wall 246.

Body 28F has an interior surface 254 bounding a bore 256 extending therethrough. Interior surface 254 comprises a cylindrical central inner wall 258, a proximal washer seat 260 formed proximal thereof, and frustoconical distal inner wall 262 formed distal thereof. Again, washer seat 260 has a diameter greater than central inner wall 258 such that a shoulder 264 is formed therebetween.

Configured to press fit within each washer seat 248, 250 and 260 is a corresponding washer 264, 265, and 266. Each washer is identical and has an annular exterior side wall 268 extending between a top face 270 and an opposing bottom face 272. Each washer also has an interior surface 274 bounding an opening 276 extending therethrough. In one embodiment, each washer is formed of a elastic metal such as nitinol. Examples of other materials that can also be used include biocompatible metals, such as titanium alloys, zirconium alloys, cobalt chromium alloys, stainless steels or combinations thereof.

During assembly, washers 264–266 are initially press fit into corresponding washer seats 248, 250, and 260. In this assembled configuration, neck 26F and body 26F in conjunction with the washers 264–266 have substantially the same configuration as neck 26B and body 28B discussed with regard to FIGS. 9 and 10. As such, Body 26F is mounted to stem 30 such that a self-locking tapered connection is formed between distal inner wall 262 of body 28F and distal stem portion 112 of stem 30. In addition, a press fit connection is formed between washer 266 and central stem portion 110 of stem 30. With regard to neck 26F, washers 264 and 265 form a press fit connection with proximal stem portion 106 and central stem portion 110 of stem 30.

Figure 19:
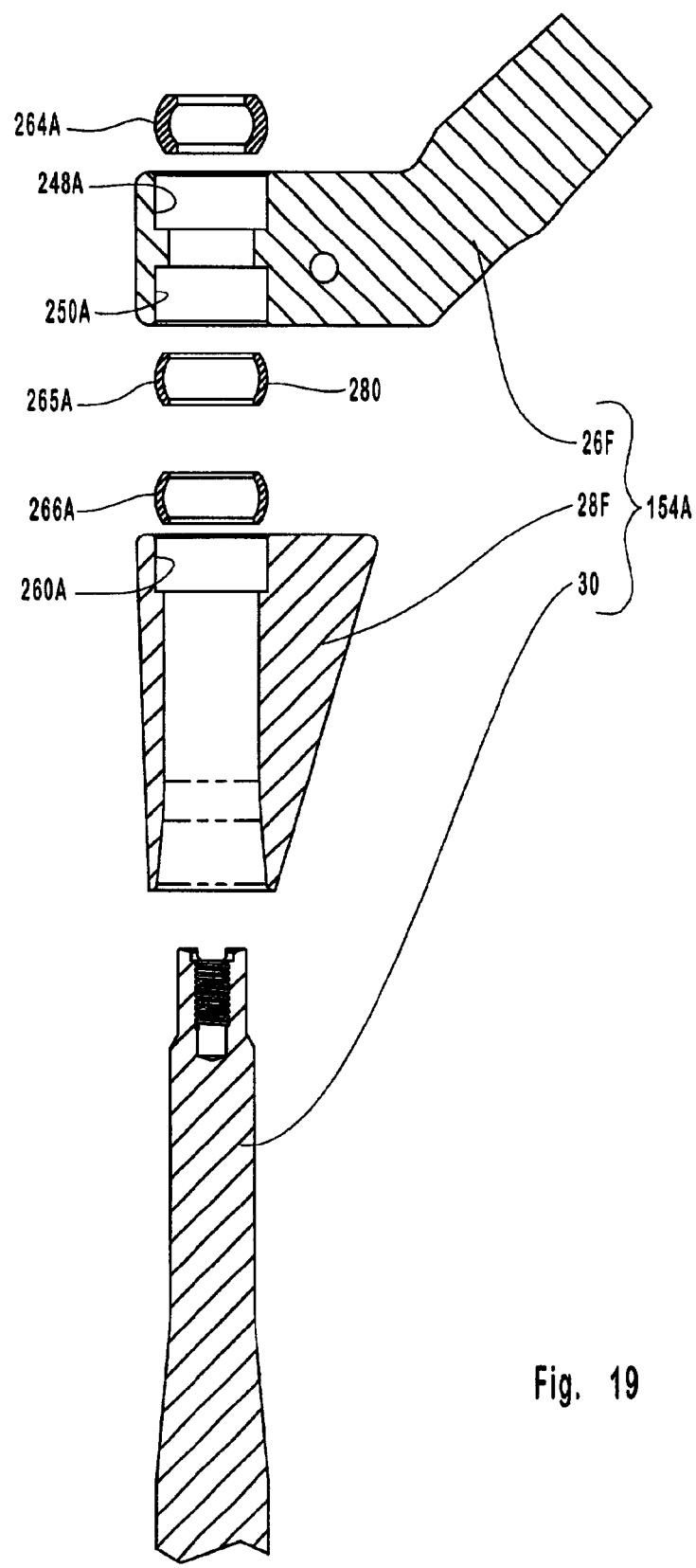
FIG. 19 is an exploded cross sectional side view of an alternative embodiment of a modular prosthesis wherein spring washers are used to press fit the neck and body to the stem.
Figure 20:
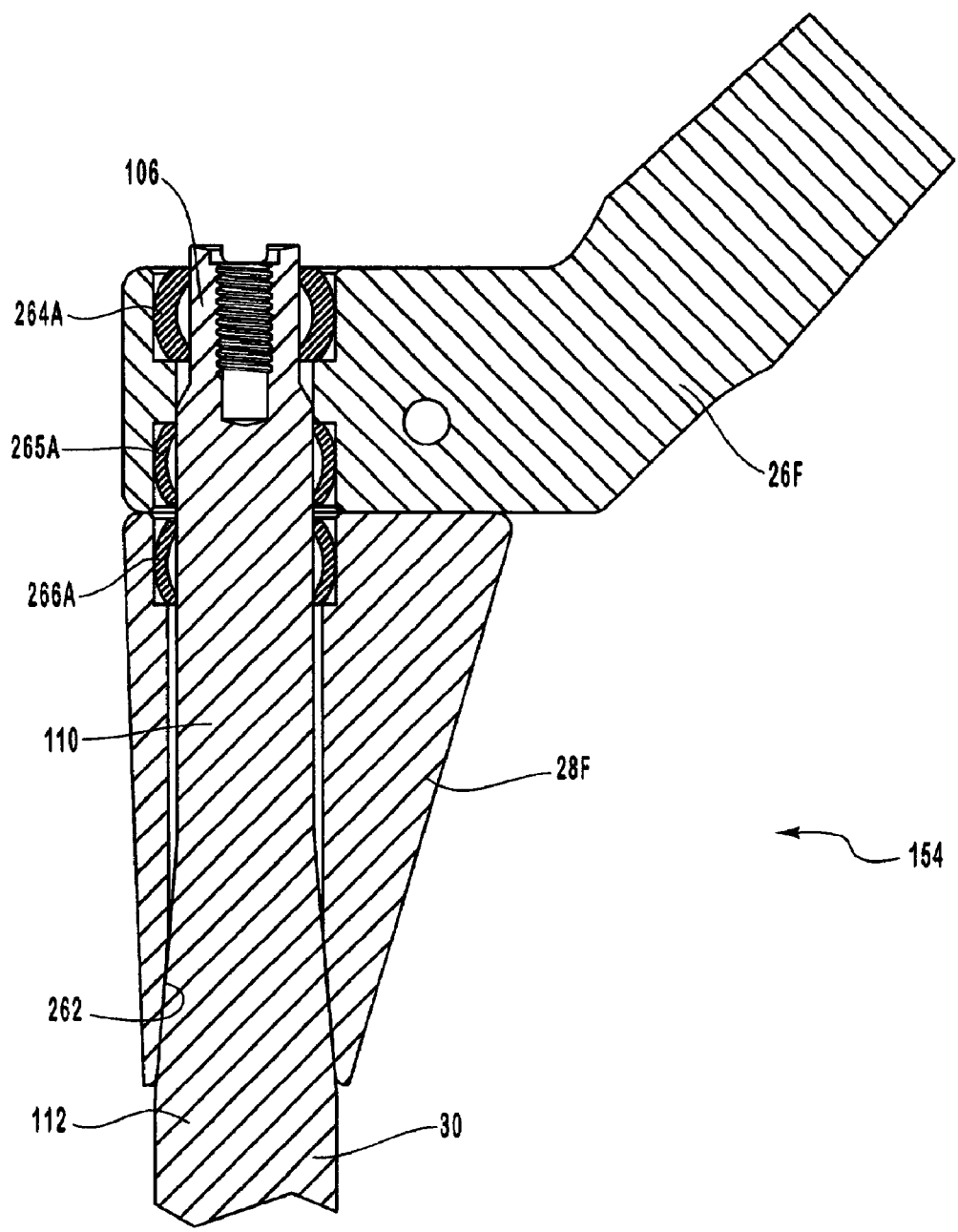
FIG. 20 is a cross sectional side view of the modular prosthesis shown in FIG. 19 in an assembled state.

Depicted in FIGS. 19 and 20 is an alternative modular prosthesis 154A which is substantially identical to modular prosthesis 154. The primary distinction between modular prosthesis 154 and 154A is that flat washers 264–266 are replaced with resiliently flexible spring washers 264A–266A. Each spring washer has an annular side wall 280 with a shallow substantially C-shaped configuration. Spring washers are configured such that when side wall 280 compressed, side wall 280 produces a resilient bias force to return to its original configuration. In general, springs washers are made from biocompatible metals, such as titanium alloys, zirconium alloys, cobalt chromium alloys, stainless steels or combinations thereof. Other materials can also be used.

Washer seats 248A, 250A, and 260A are positioned at substantially the same places as washers seats 248, 250, and 260 but are slightly larger to accommodate the increased side of the spring washers. In turn, spring washers 264A–266A function to produce press fit connections between neck 26F and stem 30 and also between body 28F and stem 30 as previously discussed with regard to modular prosthesis 154.

Figure 21:
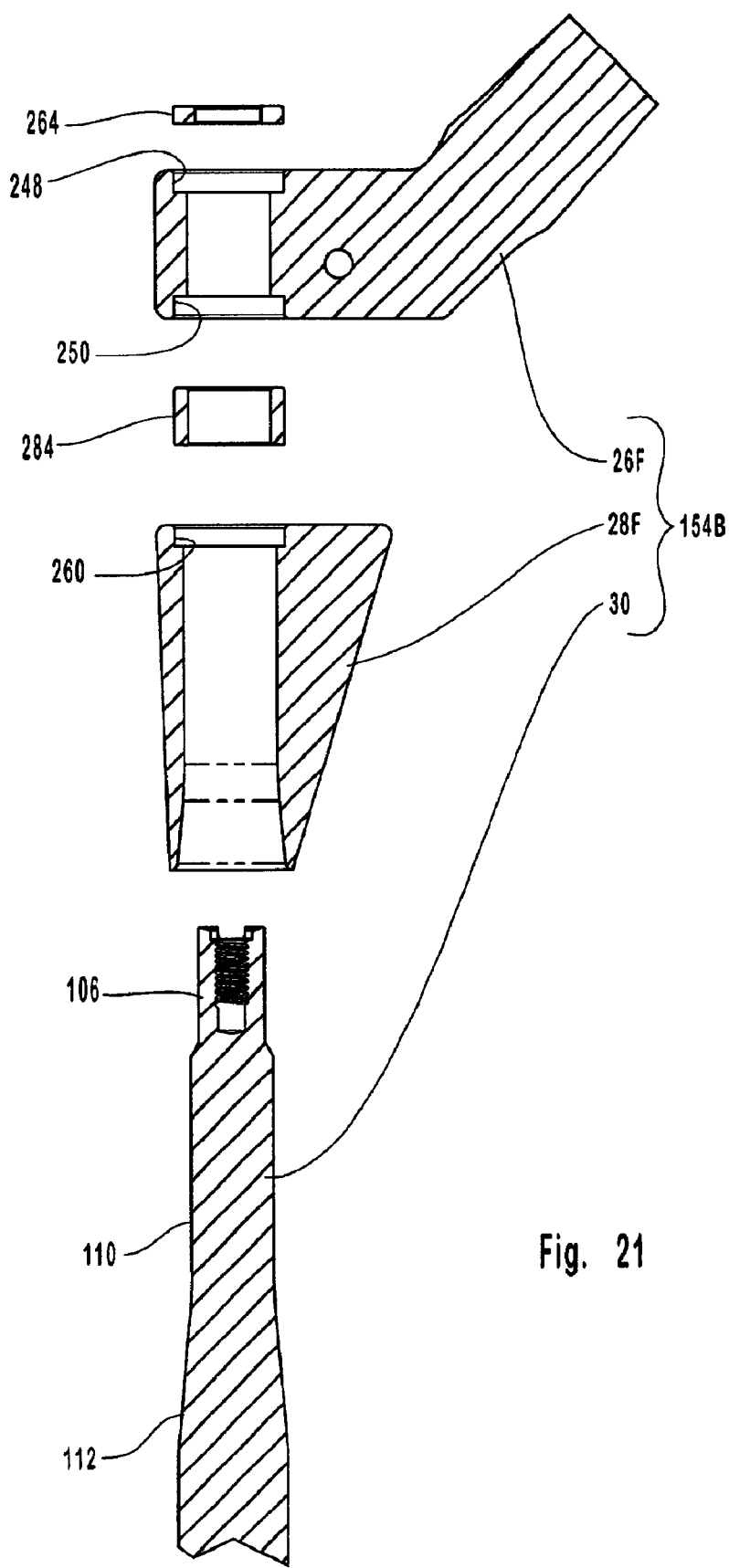
FIG. 21 is a exploded cross sectional side view of an alternative embodiment of a modular prosthesis wherein a single washer extends between the body and neck.
Figure 22:
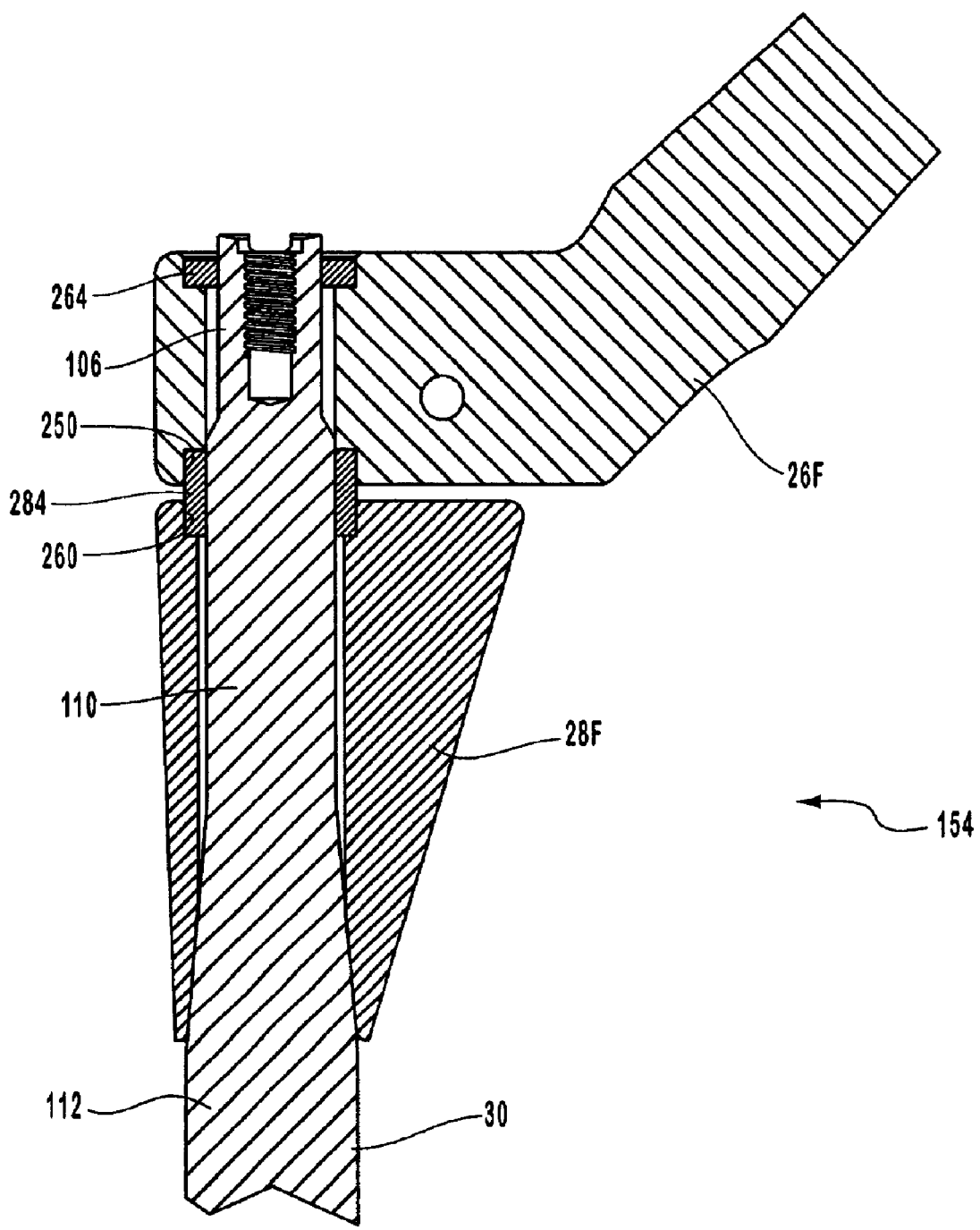
FIG. 22 is a cross sectional side view of the modular prosthesis shown in FIG. 21 in an assembled state.

Finally, depicted in FIGS. 21 and 22 is a modular prosthesis 154B. Modular prosthesis 154B is that same as modular prosthesis 154 except that separate washers 265 and 266 have been replaced with an elongated washer 284. Washer 284 press fits into both washer seats 250 and 260. Washer 284 also facilitates a press fit connection between the proximal end of body 28F and stem 30 and between the distal end of neck 26F and stem 30.

In alternative embodiments it is appreciated that where washers are used, the continuous circular washers can be replaced with a segment of a washer to two or more segments of washers.

Figure 1:
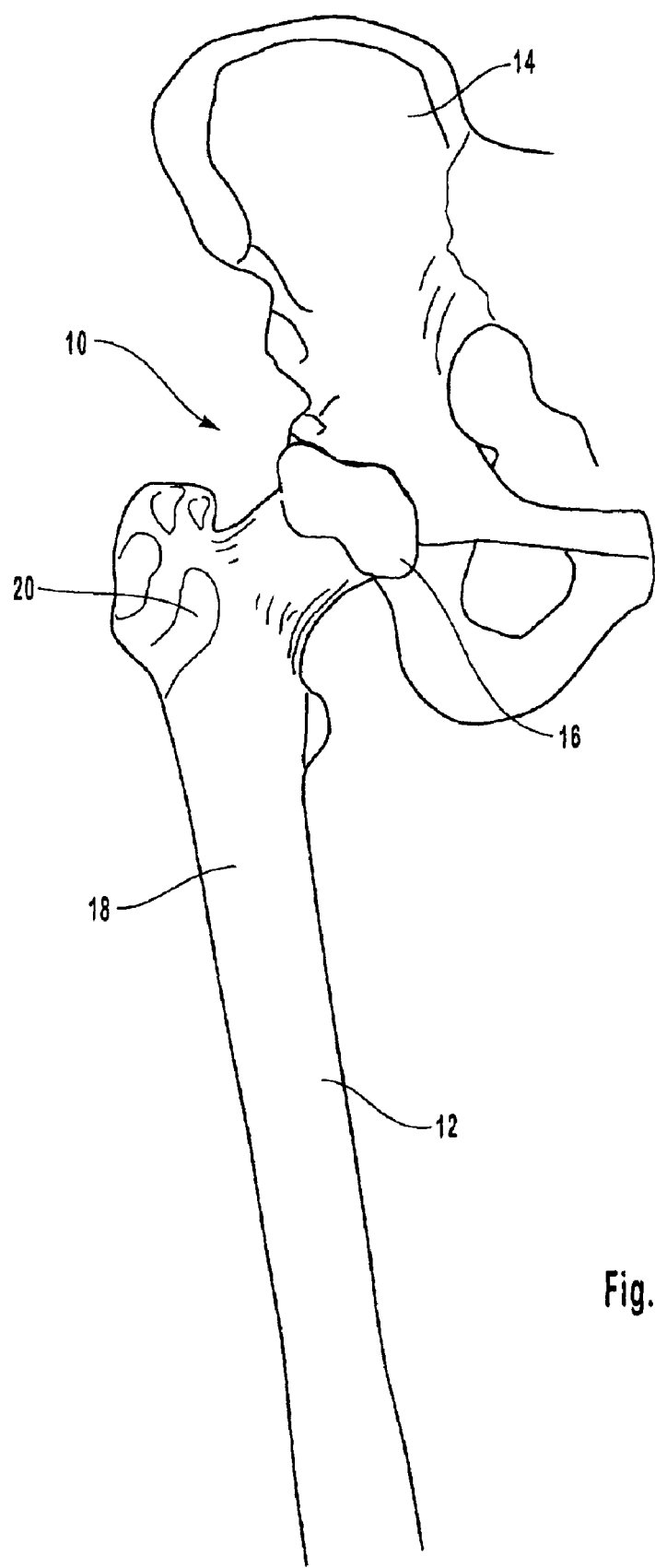
FIG. 1 is an elevated front view of a hip joint.

One example of use of the above described modular prosthesis will not be described with reference to femur 12 depicted in FIG. 1. Initially, articulating end 16 of femur 12 is removed. The distal end of stem 30 is then inserted into shaft 18 of femur 12 so that the proximal end of shaft 18 extends outside of femur 12. A body 28 of the modular prosthesis having a configuration most complementary to exposed opening on femur 12 is the passed over the proximal end of stem 30 and guided down into the metaphyseal equivalent 20 where it is connected with stem 30 using one of the removable connections described herein. In alternative embodiments, body 28 can be mounted on stem 30 prior to securing stem 30 within femur 12.

Next, a neck 26 having a desired configuration for the specific procedure is advanced over the proximal end of stem 30. Once oriented into the desired position, neck 26 is also connected to stem 30 using one of the removable connections described herein.

Although not required, one of the benefits of each of the embodiments described herein is that both the body 28 and neck 26 can be at least partially positioned on stem 30 in a close to final position and then selectively rotated relative to stem 30 so as to be in the optimal position. Once properly oriented, the select body and neck can then be further advanced on stem 30 to establish the releasable connection with stem 30.

The present invention may be embodied in other specific forms without departing from its spirit or essential characteristics. For example, various alternative releasable connections are described herein. In alternative embodiments, it is appreciated that the various connections and alternatives thereof can be mixed and matched into new combinations. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A modular prosthesis for replacing a portion of a bone having an articulating end, the modular prosthesis comprising:

a neck comprising a base having an extension projecting therefrom, the base having a first proximal end, a first distal end, and a first interior surface bounding a first bore extending through the base between the first proximal end and the first distal end thereof;

a body comprising a second proximal end, a second distal end, and a second interior surface bounding a second bore extending through the body between the second proximal end and the second distal end; and a stem having an exterior surface extending between a proximal end and an opposing distal end, the proximal end of the stem being received within the second bore of the body such that the body is directly secured to the stem by way of at least a press fit connection or a self-locking taper connection therebetween, the proximal end of the stem also being received within the first bore of the neck such that the neck is secured to the stem by a direct press fit connection therebetween.

2. A modular prosthesis as recited in claim 1, wherein the neck engages with the body by way of a press fit connection therebetween.

3. A modular prosthesis as recited in claim 1, wherein the neck is secured to the stem by a first press fit connection therebetween and a spaced apart second press fit connection therebetween.

4. A modular prosthesis as recited in claim 3, wherein a gap is formed between the interior surface of the neck and the exterior surface of the stem between the first press fit connection and the second press fit connection.

5. A modular prosthesis as recited in claim 1, wherein the proximal end of the stem terminates at a proximal end face, a threaded socket being formed on the proximal end face of the stem.

6. A modular prosthesis for replacing a portion of a bone, the bone having an articulating end, a metaphyseal equivalent, and a shaft, the modular prosthesis comprising:

a neck for replacing the articulating end of the bone, the neck comprising a base having a first proximal end, a first distal end, and a first interior surface bounding a first bore extending through the base between the first proximal end and the first distal end thereof;

a body adapted to fit into at least a portion of the metaphyseal equivalent of the bone, the body comprising a second proximal end, a second distal end, and a second interior surface bounding a second bore extending through the body between the second proximal end and the second distal end; and a stem having an exterior surface extending between a proximal end and an opposing distal end, the distal end of the stem being adapted to fit into at least a portion of the shaft of the bone, the proximal end of the stem being received within the second bore of the body and the first bore of the neck, the exterior surface of the stem biasing in frictional engagement directly against the first interior surface of the neck at a first neck location positioned at the proximal end of the neck and at a second neck location positioned at the distal end of the neck so that the neck is securely held to the stem, a gap being formed between the exterior surface of the stem and the first interior surface of the neck along at least a portion of the distance between the first neck location and the second neck location, the second interior surface of the body engaging at least a portion of the exterior surface of the stem by way of at least either a releasable press fit connection or a releasable self-locking tapered fit connection therebetween.

7. A modular prosthesis as recited in claim 6, wherein the exterior surface of the stem biases in frictional engagement directly against the first interior surface of the neck at the first neck location by way of a press fit connection therebetween.

8. A modular prosthesis as recited in claim 6, wherein the exterior surface of the stem biases in frictional engagement directly against the first interior surface of the neck at the second neck location by way of a press fit connection or a self-locking taper connection therebetween.

9. A modular prosthesis as recited in claim 6, wherein the first interior surface of the neck comprises:

a central boundary wall having a maximum outer diameter;

a proximal boundary wall positioned proximal of the central boundary wall, the proximal boundary wall having a maximum outer diameter smaller than the maximum outer diameter of the central boundary wall; and a distal boundary wall positioned distal of the central boundary wall, the distal boundary wall having a maximum outer diameter larger than the maximum outer diameter of the central boundary wall.

10. A modular prosthesis as recited in claim 9, wherein the proximal boundary wall and the distal boundary wall each have a substantially cylindrical configuration.

11. A modular prosthesis as recited in claim 9, wherein the distal boundary wall has a substantially frustoconical configuration.

12. A modular prosthesis as recited in claim 9, wherein the proximal end of the stem comprises:

a first stem segment located at the proximal end of the stem, the first stem segment biasing in direct frictional engagement against the proximal boundary wall of the neck, the first stem segment of the stem having a maximum outer diameter; and a second stem segment located distal of the first stem segment, the second stem segment biasing in direct frictional engagement against the distal boundary wall of the neck, the second stem segment having a maximum outer diameter larger than the maximum outer diameter of the first stem segment.

13. A modular prosthesis as recited in claim 6, wherein the gap circles about the exterior surface of the stem.

14. A modular prosthesis as recited in claim 6, wherein the gap extends along the length of the stem at a distance in a range between about 5 mm to about 25 mm.

15. A modular prosthesis as recited in claim 6, wherein the neck further comprises a post extending from the base.

16. A modular prosthesis as recited in claim 6, wherein the neck is either biased against or spaced apart from the body.

17. A modular prosthesis as recited in claim 15, wherein the post further comprises a frustoconical surface formed to provide selective attachment to a spherical head.

18. A modular prosthesis for replacing a portion of a bone, the bone having an articulating end, a metaphyseal equivalent, and a shaft, the modular prosthesis comprising:

a neck for replacing the articulating end of the bone, the neck comprising:

a base having a first proximal end, a first distal end, and a first interior surface bounding a first bore extending through the base between the first proximal end and the first distal end thereof, and a post projecting from the base, the post having a frustoconical surface;

a body adapted to fit into at least a portion of the metaphyseal equivalent of the bone, the body comprising a second proximal end, a second distal end, and a second interior surface bounding a second bore extending through the body between the second proximal end and the second distal end; and a stem having an exterior surface extending between a proximal end and an opposing distal end, the distal end of the stem being adapted to fit into at least a portion of the shaft of the bone, the proximal end of the stem being received within the second bore of the body and the first bore of the neck, the exterior surface of the stem biasing in frictional engagement directly against the second interior surface of the body at a first body location positioned at the proximal end of the body and at a second body location positioned at the distal end of the body so that the body is securely held to the stem, a gap being formed between the exterior surface of the stem and the second interior surface of the body along at least a portion of the distance between the first body location and the second body location.

19. A modular prosthesis as recited in claim 18, wherein the exterior surface of the stem biases in frictional engagement directly against the second interior surface of the body at the first body location by way of a press fit connection or a self-locking taper connection therebetween.

20. A modular prosthesis as recited in claim 18, wherein the exterior surface of the stem biases in frictional engagement directly against the second interior surface of the body at the second body location by way of a press fit connection or a self-locking taper connection therebetween.

21. A modular prosthesis as recited in claim 18, wherein the gap circles about the exterior surface of the stem.

22. A modular prosthesis as recited in claim 18, wherein the gap extends along the length of the stem at a distance in a range between about 10 mm to about 50 mm.

23. A modular prosthesis as recited in claim 18, wherein the neck is either biased against or spaced apart from the body.

24. A modular prosthesis as recited in claim 18, wherein the neck engages with the stem by way of at least a press fit connection.

25. A modular prosthesis for replacing a portion of a bone having an articulating end, the modular prosthesis comprising:
 a neck comprising a base having an extension projecting therefrom, the base having a first proximal end, a first distal end, a first interior surface bounding a first bore extending through the base between the first proximal end and the first distal end thereof;
 a body comprising a second proximal end, a second distal end, and a second interior surface bounding a second bore extending through the body between the second proximal end and the second distal end;
 a stem having an exterior surface extending between a proximal end and an opposing distal end, the proximal end of the stem being received within the second bore of the body and the first bore of the neck, a select one of the neck or the body biasing against the other of the neck or the body so as to frictionally secure the other of the neck or the body directly to the stem;
 a first rim projecting from a distal end face of the neck or a proximal end face of the body; and
 a second rim projecting from the other of the distal end face of the neck or the proximal end face of the body, the first rim biasing against the second rim so as to radially inwardly bias the second rim against the stem.

26. A modular prosthesis as recited in claim 25, wherein the neck is coupled with the body by way of a press fit connection, the press fit connection between the neck and body causing a portion of the body to frictionally engage against the stem.

27. A modular prosthesis as recited in claim 25, further comprising the proximal end of the neck being coupled with the stem by way of a press fit connection.

28. A modular prosthesis as recited in claim 25, further comprising the distal end of the body being coupled with the stem by way of a press fit connection or a self-locking taper connection.

29. A modular prosthesis for replacing a portion of a bone, the bone having an articulating end, a metaphyseal equivalent, and a shaft, the modular prosthesis comprising:
 a neck for replacing the articulating end of the bone, the neck comprising a base having a first proximal end, a first distal end, and a first interior surface bounding a first bore extending through the base between the first proximal end and the first distal end thereof, the first interior surface comprising a proximal boundary wall having a maximum outer diameter and a distal boundary wall having a maximum outer diameter larger than the maximum outer diameter of the proximal boundary wall, the proximal boundary wall and the distal boundary wall each having a substantially cylindrical configuration;
 a body adapted to fit into at least a portion of the metaphyseal equivalent of the bone, the body comprising a second proximal end, a second distal end, and a second interior surface bounding a second bore extending through the body between the second proximal end and the second distal end;
 a stem having an exterior surface extending between a proximal end and an opposing distal end, the distal end of the stem being adapted to fit into at least a portion of the shaft of the bone, the proximal end of the stem being received within the second bore of the body and the first bore of the neck, the exterior surface of the stem biasing in frictional engagement directly against the first interior surface of the neck at a first neck location positioned at the proximal end of the neck and at a second neck location positioned at the distal end of the neck so that the neck is securely held to the stem, a gap being formed between the exterior surface of the stem and the first interior surface of the neck along at least a portion of the distance between the first neck location and the second neck location.

30. A modular prosthesis as recited in claim 29, wherein the exterior surface of the stem biases in frictional engagement directly against the first interior surface of the neck at the first neck location by way of a press fit connection therebetween.

31. A modular prosthesis as recited in claim 29, wherein the exterior surface of the stem biases in frictional engagement directly against the first interior surface of the neck at the second neck location by way of a press fit connection or a self-locking taper connection therebetween.

32. A modular prosthesis as recited in claim 29, where in the proximal end of the stem comprises:
 a first stem segment located at the proximal end of the stem, the first stem segment biasing in direct frictional engagement against the proximal boundary wall of the neck, the first stem segment of the stem having a maximum outer diameter; and
 a second stem segment located distal of the fisrt stem segment, the second stem segment biasing in direct frictional engagement against the distal boundary wall of the neck, the second stem segment having maximum outer diameter larger than the maximum outer diameter of the first stem segment.

33. A modular prosthesis as recited in claim 29, wherein the gap circles about the exterior surface of the stem.

34. A modular prosthesis as recited in claim 29, wherein the neck further comprises a post extending from the base.

35. A modular prosthesis as recited in claim 34, wherein the post further comprises a frustoconical surface.

* * * * *

UNITED STATES PATENT AND TRADEMARK OFFICE
CERTIFICATE OF CORRECTION

PATENT NO.         : 6,875,239 B2
APPLICATION NO. : 10/132671
DATED                   : April 5, 2005
INVENTOR(S)        : Daniel E. Gerbec et al.

It is certified that error appears in the above-identified patent and that said Letters Patent is hereby corrected as shown below:

Column 1, Line 19 (background of the invention) Delete "One" and ADD --On-- after "transitions therebetween."

Col. 1, line 31, (background of the invention) Delete "space" in between "of" and "ten" Should read --it is often difficult--

Col. 5, line 51, (detailed description) Delete "surface" and ADD --surfaces--

Col. 10, line 19, (detailed description) Delete "not" and ADD --now--

Col. 10, line 25, (detailed description) Delete "the" and ADD --then-- after "femur 12 is" and before "passed over"

Col. 14, line 53 (claim 32) Delete "fisrt" and ADD --first--

Signed and Sealed this

Twenty-third Day of January, 2007

JON W. DUDAS
*Director of the United States Patent and Trademark Office*